(12) United States Patent
El Katerji et al.

(10) Patent No.: US 11,581,083 B2
(45) Date of Patent: Feb. 14, 2023

(54) INTRA-AORTIC PRESSURE FORECASTING

(71) Applicants: Abiomed, Inc., Danvers, MA (US); Northeastern University, Boston, MA (US)

(72) Inventors: Ahmad El Katerji, Danvers, MA (US); Erik Kroeker, Danvers, MA (US); Elise Jortberg, Danvers, MA (US); Rose Yu, Boston, MA (US); Rui Wang, Boston, MA (US)

(73) Assignees: Abiomed, Inc., Danvers, MA (US); Northeastern University, Boston, MA (US)

( * ) Notice: Subject to any disclaimer, the term of this patent is extended or adjusted under 35 U.S.C. 154(b) by 315 days.

(21) Appl. No.: 16/889,457

(22) Filed: Jun. 1, 2020

(65) Prior Publication Data
US 2020/0376183 A1 Dec. 3, 2020

Related U.S. Application Data

(60) Provisional application No. 62/855,389, filed on May 31, 2019.

(51) Int. Cl.
*G06F 9/44* (2018.01)
*G06F 9/455* (2018.01)
(Continued)

(52) U.S. Cl.
CPC .......... *G16H 20/40* (2018.01); *A61M 5/1723* (2013.01); *A61M 60/13* (2021.01);
(Continued)

(58) Field of Classification Search
CPC ..... G16H 20/40; G06N 20/00; A61M 60/585; A61M 60/531; A61M 60/829;
(Continued)

(56) References Cited

U.S. PATENT DOCUMENTS 10,857,275 B2 * 12/2020 Granegger .......... A61M 60/216
11,338,125 B2 *  5/2022 Liu .................... A61M 60/178
(Continued)

FOREIGN PATENT DOCUMENTS

EP      3287154 A1   2/2018
WO   2018039458 A1   3/2018

OTHER PUBLICATIONS

Shishvan et al., Machine Intelligence in Healthcare and Medical Cyber Physical Systems: A Survey, 76 pages (Year: 2018).*
(Continued)

*Primary Examiner* — Thuy Dao
(74) *Attorney, Agent, or Firm* — Botos Churchill IP Law LLP

(57) ABSTRACT

Aspects of the present disclosure describe systems and methods for predicting an intra-aortic pressure of a patient receiving hemodynamic support from a transvalvular micro-axial heart pump. In some implementations, an intra-aortic pressure time series is derived from measurements of a pressure sensor of the transvalvular micro-axial heart pump and a motor speed time series is derived from a measured back electromotive force of a motor of the transvalvular micro-axial heart pump. Furthermore, in some implementations, machine learning algorithms, such as deep learning, are applied to the intra-aortic pressure and motor speed time series to accurately predict an intra-aortic pressure of the patient. In some implementations, the prediction is short-term (e.g., approximately 5 minutes in advance).

27 Claims, 25 Drawing Sheets

(51) Int. Cl.

| | |
|---|---|
| A61M 60/50 | (2021.01) |
| G06N 5/04 | (2006.01) |
| G16H 20/40 | (2018.01) |
| G06N 20/00 | (2019.01) |
| A61M 5/172 | (2006.01) |
| A61M 60/13 | (2021.01) |
| A61M 60/174 | (2021.01) |
| A61M 60/422 | (2021.01) |
| A61M 60/88 | (2021.01) |
| A61M 60/857 | (2021.01) |
| A61M 60/531 | (2021.01) |
| A61M 60/829 | (2021.01) |
| A61M 60/585 | (2021.01) |
| A61M 60/894 | (2021.01) |
| A61M 60/216 | (2021.01) |
| G06N 3/08 | (2023.01) |

(52) U.S. Cl.
CPC ........ *A61M 60/174* (2021.01); *A61M 60/216* (2021.01); *A61M 60/422* (2021.01); *A61M 60/531* (2021.01); *A61M 60/585* (2021.01); *A61M 60/829* (2021.01); *A61M 60/857* (2021.01); *A61M 60/88* (2021.01); *A61M 60/894* (2021.01); *G06N 20/00* (2019.01); *A61M 2205/3331* (2013.01); *A61M 2205/3365* (2013.01); *A61M 2205/50* (2013.01); *G06N 3/08* (2013.01)

(58) Field of Classification Search
CPC .. A61M 60/894; A61M 60/13; A61M 60/422; A61M 60/174; A61M 60/88; A61M 60/857; A61M 60/216; A61M 5/1723

See application file for complete search history.

(56) References Cited

U.S. PATENT DOCUMENTS

| | | |
|---|---|---|
| 2004/0022640 A1 | 2/2004 | Siess et al. |
| 2016/0000983 A1 | 1/2016 | Mohl et al. |
| 2018/0078159 A1 | 3/2018 | Edelman et al. |
| 2018/0353667 A1 | 12/2018 | Moyer et al. |

OTHER PUBLICATIONS

Amjad et al., Estimation of velocity and pressure profiles to design an optimum Von Karman Viscous Pump, 8 pages (Year: 2017).*

Abbasi et al., Long-term Prediction of Blood Pressure Time Series Using Multiple Fuzzy Functions, 21st Iranian Conference on Biomedical Engineering, ICBME, 2014.

Abiomed, Impella® Ventricular Support Systems for Use During Cardiogenic Shock and High-Risk PCI: Instructions for Use and Clinical Reference Manual, Document No. 0042-9028 rG (Apr. 2020).

Bahdanau et al., Neural Machine Translation by Jointly Learning to Align and Translate, arXiv:1409.0473v7, 2016.

Bai et al., An Empirical Evaluation of Generic Convolutional and Recurrent Networks for Sequence Modeling, arXiv:1803.01271v2, 2018.

Bergstra & Bengio, Random Search for Hyper-Parameter Optimization, Journal of Machine Learning Research 13 281-305, 2012.

Chemla et al., Mean aortic pressure is the geometric mean of systolic and diastolic aortic pressure in resting humans, Journal of Applied Physiology 99:6, 2278-2284, 2005.

Deo & Nallamothu, Learning About Machine Learning: The Promise and Pitfalls of Big Data and the Electronic Health Record, Circ. Cardiovasc. Qual. Outcomes, 9:618-620, 2016.

Dixon et al., A prospective feasibility trial investigating the use of the Impella 2.5 System in Patients Undergoing High-Risk Percutaneous Coronary Intervention (The Protect I Trial), JACC Cardiovasc Interv. 2 (2) 91-96, 2009.

Dunser et al., Arterial blood pressure during early sepsis and outcome, Intensive Care Med. 35:1225-1233, 2009.

Dunser et al., Association of arterial blood pressure and vasopressor load with septic shock mortality: a post hoc analysis of a multicenter trial, Crit. Care Lond. Engl. 13:R181, 2009.

Harutyunyan et al., Multitask learning and benchmarking with clinical time series data, Scientific Data, doi: 10.1038/s41597-019-0103-9, 2017.

Hatib et al., Machine-learning Algorithm to Predict Hypotension Based on High-Fidelity Arterial Pressure Waveform Analysis, Anesthesiology, 129(4):663-674, 2018.

International Search Report and Written Opinion for Application No. PCT/US2020/070103 dated Sep. 7, 2020.

Johnson et al., MIMIC-III, a freely accessible critical care database, Scientific Data, DOI: 10.1038/sdata.2016.35, 2016.

Kenney et al., Early Detection of Heart Failure Using Electronic Health Records, Circ. Cardiovasc. Qual. Outcomes, 9:649-658, 2016.

Luong et al., Effective Approaches to Attention-based Neural Machine Translation, arXiv:1508.04025, 2015.

Moody & Lehman, Predicting Acute Hypotensive Episodes: The 10th Annual PhysioNet/Computers in Cardiology Challenge, Comput. Cardiol., 36(5445351): 541-544, 2009.

O'Neill et al., A pros., random. clin. trial of hemodyn.supp. with transvalv. micro-axial heart pump v. intra-aortic ball. pump in pat. under, high-risk precut. cor. interven.: the transvalv. micro-axial heart pump study, Circ. 126 (14) 1717-1727, 2012.

Passantino et al., Predicting mortality in patients with acute heart failure: Role of risk scores, World J. Cardiol., 7(12): 902911, 2015.

Peng et al., Long-term Blood Pressure Prediction with Deep Recurrent Neural Networks, arXiv:1705.04524v3, 2018.

Purushothama et al., Benchmarking deep learning models on large healthcare datasets, Journal of Biomedical Informatics 83, 112-134, 2018.

Schmidhuber, Deep Learning in Neural Networks: An Overview, arXiv:1404.7828v4, 2014.

Shen et al., Convolutional Neural Pyramid for Image Processing, arXiv:1704.02071v1 [cs.CV], 2017.

Sutskever et al., Sequence to Sequence Learning with Neural Networks, NeurIPS 2014.

Thorvaldsen et al., Predicting Risk in Patients Hospitalized for Acute Decompensated Heart Failure and Preserved Ejection Fraction, Circ. Heart Fail., 10:e003992, 2017.

Vaswani et al., Attention Is All You Need, arXiv:1706.03762v5, 2017.

Voelker et al., Legendre Memory Units: Continuous-Time Representation in Recurrent Neural Networks, NeurIPS 2019.

Wijnberge Eff. of a Mach. Learn.-Der. Early Warn. Sys. for Intraop. Hypoten. vs Stand. Care on Dep. and Dur. of Intraop. Hypoten. During Elect. Noncard. Surg: The HYPE Ran. Clin. Tri., JAMA, Caring for the Crit. Ill Pat., doi:10.1001/jama.2020.0592, 2020.

Burkhoff & Naidu, "The science behind percutaneous hemodynamic support: a review and comparison of support strategies,", Catheter Cardiovasc Interv. 80:, 2012, 816-29.

Russo, et al., "Hemodynamics and its predictors during transvalvular-micro-axial-heart-pump-protected PCI in high risk patients with reduced ejection fraction", Int. J. Cardiol. 274:, 2019, 221-225.

Tang, Hong, et al., "A non-invasive approach to investigation of ventricular blood pressure using cardiac sound features", Physiological Measurement, Institute of Physics Publishing, Bristol, GB, vol. 38, No. 2, Jan. 18, 2017, pp. 289-309, XP020312898, ISSN: 0967-3334, DOI: 10.1088/1361-6579/AA552A [retrieved on Jan. 18, 2017] abstract.

Varpula, et al., "Hemodynamic variables related to outcome in septic shock,", Intensive Care Med. 31:, 2005, 1066-1071.

Givertz et al., Acute Decompensated Heart Failure: Update on New and Emerging Evidence and Directions for Future Research, Journal of Cardiac Failure, vol. 19, No. 6, 2013.

Henriques & Rocha, Prediction of Acute Hypotensive Episodes Using Neural Network Multi-models, Computers in Cardiology 36:549552, 2009.

Hochreiter & Schmidhuber, Long Short-Term Memory, Neural Computation, vol. 9, Issue 8, 1997.

(56) References Cited

OTHER PUBLICATIONS

Hyndman & Athanasopoulos, Forecasting: principles and practice, 2nd edition, Chapter 8 ARIMA models, OTexts Melbourne, Australia, OTexts.com/fpp2, 2018.

Wijnberge, Eff. of a Mach. Learn.-Der. Early Warn. Sys. for Intraop. Hypoten. vs Stand. Care on Dep. and Dur. of Intraop. Hypoten. During Elect. Noncard. Surg: The HYPE Ran. Clin. Tri., JAMA, Caring for the Crit. Ill Pat., doi:10.1001/jama.2020.0592, 2020.

Russo, et al., "Hemodynamics and its predictors during transvalvular-micro-axial-heart-pump-protected PCI in high risk patients with reduced ejection fraction", Inf J. Cardiol 274:, 2019, 221-225.

\* cited by examiner

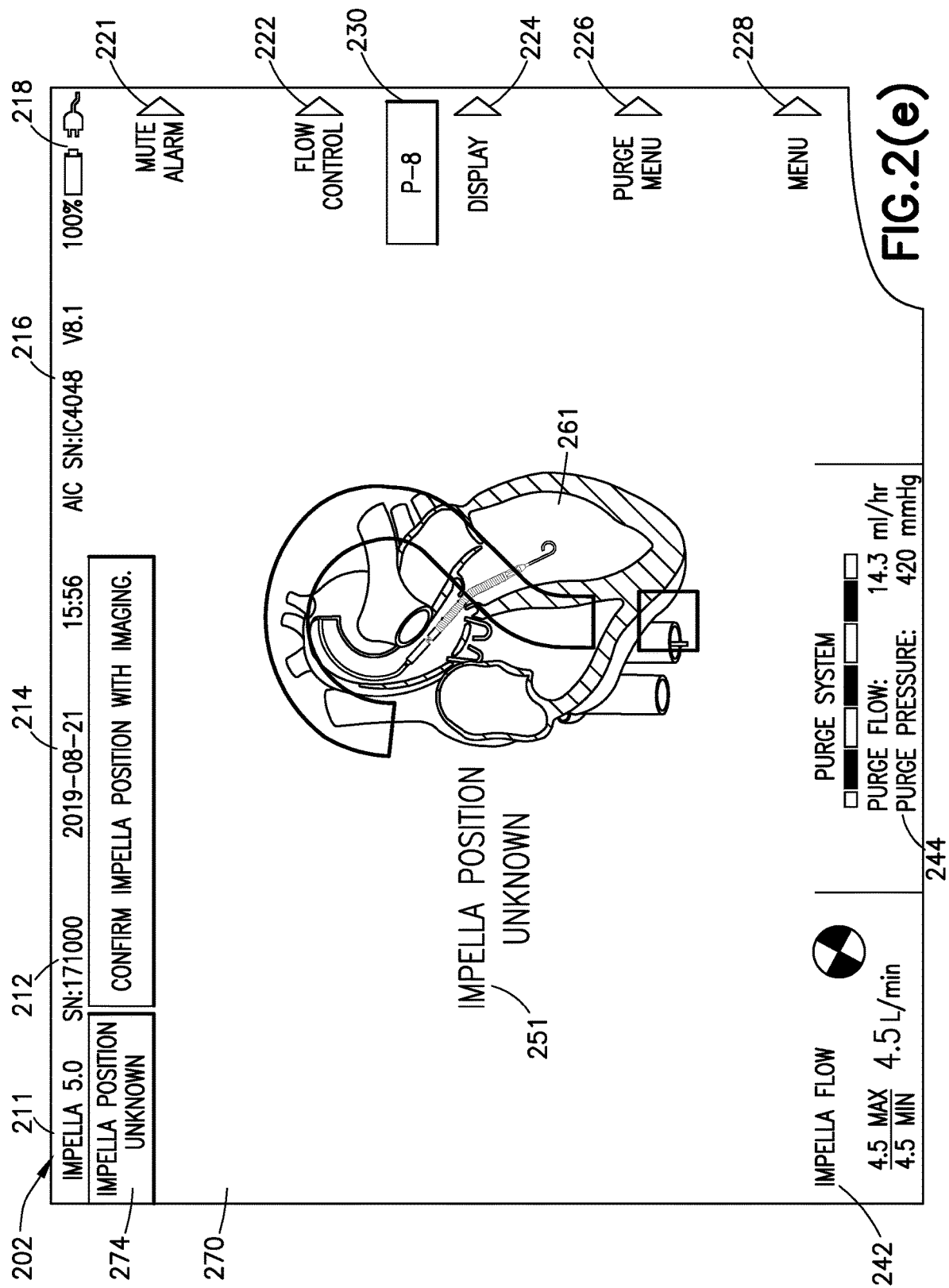

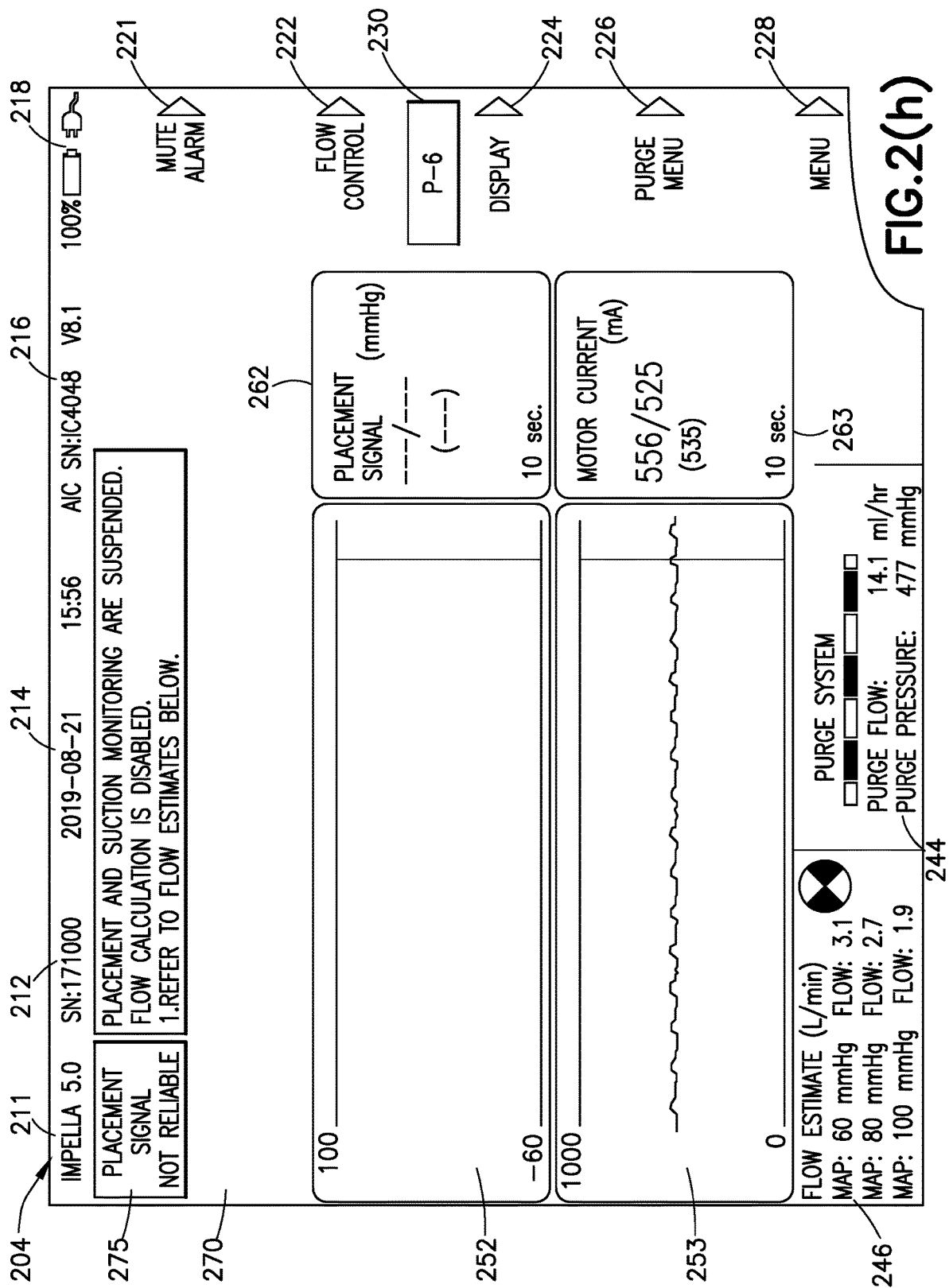

| FIG.15A |
|---|
| FIG.15B |

INTRA-AORTIC PRESSURE FORECASTING

CROSS-REFERENCE TO RELATED APPLICATIONS

This application claims the benefit of the U.S. Provisional Application No. 62/855,389, which was filed on May 31, 2019 and is incorporated herein by reference.

TECHNICAL FIELD

The present technology relates to systems and methods for predicting an intra-aortic pressure of a patient receiving hemodynamic support from a transvalvular micro-axial heart pump.

BACKGROUND

Machine learning has been successfully applied in a variety of different technical fields, such as computer vision, natural language processing, speech recognition, and clinical healthcare, to provide predictions. Examples of machine learning algorithms include Bayesian algorithms, clustering algorithms, decision tree algorithms, dimensionality reduction algorithms, instance-based algorithms, deep learning algorithms, regression algorithms, regularization algorithms, and rule-based machine learning algorithms. In clinical healthcare, machine learning algorithms have been used for modeling risk of mortality, forecasting length of stay, detecting physiologic decline, and classifying phenotypes. See, e.g., Harutyunyan et al., *Multitask learning and benchmarking with clinical time series data*, Scientific Data, doi: 10.1038/s41597-019-0103-9, 2017; Purushothama et al., *Benchmarking deep learning models on large healthcare datasets*, Journal of Biomedical Informatics 83, 112-134, 2018. However, there remains a need for systems and methods for predicting physiological responses, which could help physicians with real-time early detection of diseases and patient response to therapies.

BRIEF SUMMARY

Heretofore, machine learning algorithms have not been used to predict an intra-aortic pressure (e.g., current intra-aortic pressure, mean intra-aortic pressure, median intra-aortic pressure, maximum intra-aortic pressure, minimum intra-aortic pressure, range of intra-aortic pressure, intra-aortic pressure during systole, intra-aortic pressure during diastole, etc.) of a patient receiving hemodynamic support. Forecasting the intra-aortic pressure of a patient is challenging, in part, because a high frequency intra-aortic blood pressure time series is not currently publicly available. Furthermore, an intra-aortic blood pressure time series can be noisy and highly non-stationary. Moreover, forecasting error and uncertainty grows drastically for long-term forecasting.

The ability to predict an intra-aortic pressure of a patient would greatly enhance the ability of clinicians to forecast the condition of the patient. For example, acute decompensated heart failure (ADHF) is a complex clinical event associated with excess morbidity and mortality, which is generally indicated by a rapid decline in blood pressure, associated with an increase in heart rate. The challenge of ADHF is the lack of effective treatments that both reduce symptoms and improve clinical outcomes. Existing guideline recommendations are largely based on expert opinion. See, e.g., Givertz et al., *Acute Decompensated Heart Failure: Update on New and Emerging Evidence and Directions for Future Research*, Journal of Cardiac Failure, Vol. 19, No. 6, 2013. Thus, being able to predict the trajectory of an intra-aortic pressure of a patient would make it easier for medical practitioners to evaluate the patient's risk of ADHF and intervene prior to collapse. In addition, intra-aortic pressure forecasting would provide helpful guidance for weaning patients off support as their health improves.

Aspects of the present disclosure describe systems and methods for predicting an intra-aortic pressure of a patient receiving hemodynamic support from a transvalvular micro-axial heart pump. In some implementations, an intra-aortic pressure time series is derived from measurements of a pressure sensor of the transvalvular micro-axial heart pump and a motor speed time series is derived from a measured back electromotive force (EMF) of a motor of the transvalvular micro-axial heart pump. Furthermore, in some implementations, machine learning algorithms, such as deep learning, are applied to the intra-aortic pressure and motor speed time series to accurately predict an intra-aortic pressure of the patient. In some implementations, the prediction is short-term (e.g., approximately 5 minutes in advance).

One aspect of the present disclosure relates to a system including a transvalvular micro-axial heart pump and one or more processors. The transvalvular micro-axial heart pump includes a motor and a pressure sensor. The one or more processors are configured to: obtain a set of intra-aortic pressure measurements corresponding to pressure values measured by the pressure sensor during a period of time when the transvalvular micro-axial pump is at least partially located in a patient's heart, obtain a set of motor speed measurements corresponding to rotational speeds of the motor during the period of time, predict, using a trained machine learning model, an intra-aortic pressure of a patient based on the sets of intra-aortic pressure and motor speed measurements, and automatically adjust a speed setting of the motor based on the predicted intra-aortic pressure of the patient.

In some implementations, the one or more processors are further configured to obtain a set of current measurements corresponding to an energy intake of the motor during the period of time, and the prediction is further based on the set of current measurements.

In some implementations, the transvalvular micro-axial heart pump further includes a tube, an inlet area having one or more openings through which blood may be drawn into the tube by the motor, and an outlet area having one or more openings through which blood may be expelled from the tube by the motor, and the pressure sensor is coupled to the outlet area. In some implementations, the transvalvular micro-axial heart pump further includes an additional pressure sensor coupled to the inlet area, the one or more processors are further configured to obtain a set of left ventricular pressure measurements corresponding to pressure values measured by the additional pressure sensor during the period of time, and the prediction is further based on the set of left ventricular pressure measurements.

In some implementations, the machine learning model is a deep learning model. In some implementations, the deep learning model is an Autoregressive Integrated Moving Average (ARIMA) model, a Deep Neural Network (DNN) model, a Recurrent Sequence to Sequence model, a Recurrent Sequence to Sequence model with Attention, a Transformer model, a Temporal Convolutional Neural Network (TCN) model, or a Convolutional Neural Pyramid model. In some implementations, the deep learning model is a Recurrent Sequence to Sequence model with a Legendre Memory Unit (LMU).

In some implementations, the machine learning model is trained on a data set having increasing sequences, decreasing sequences, and stationary sequences, wherein each sequence includes intra-aortic pressure and motor speed measurements. In some implementations, a sequence is increasing if the intra-aortic pressure measurements within that sequence increase by more than a predetermined threshold, a sequence is decreasing if the intra-aortic pressure measurements within that sequence decrease by more than the predetermined threshold, and a sequence is stationary if the intra-aortic pressure measurements within that sequence do not increase or decrease by more than the predetermined threshold. In some implementations, the predetermined threshold is 10 mmHg. In some implementations, each sequence includes a predetermined number of aortic pressure and motor speed measurements. In some implementations, each sequence includes real-time (RT) intra-aortic pressure and motor speed measurements. In some implementations, each sequence includes average time (AT) intra-aortic pressure and motor speed measurements.

In some implementations, the machine learning model is trained on a data set having only increasing and decreasing sequences, wherein each sequence includes intra-aortic pressure and motor speed measurements. In some implementations, a sequence is increasing if the intra-aortic pressure measurements within that sequence increase by more than a predetermined threshold, and a sequence is decreasing if the intra-aortic pressure measurements within that sequence decrease by more than the predetermined threshold. In some implementations, the predetermined threshold is 10 mmHg. In some implementations, each sequence includes a predetermined number of aortic pressure and motor speed measurements. In some implementations, each sequence includes real-time (RT) intra-aortic pressure and motor speed measurements. In some implementations, each sequence includes average time (AT) intra-aortic pressure and motor speed measurements.

In some implementations, automatically adjusting the speed setting of the motor based on the predicted intra-aortic pressure of the patient includes temporarily increasing the speed setting of the motor when the predicted intra-aortic pressure of the patient is less than a current intra-aortic pressure of the patient by more than a predetermined amount.

Another aspect of the present disclosure relates to a system including a transvalvular micro-axial heart pump, one or more processors, and a display. The transvalvular micro-axial heart pump includes a motor and a pressure sensor. The one or more processors are configured to: obtain a set of intra-aortic pressure measurements corresponding to pressure values measured by the pressure sensor during a period of time when the transvalvular micro-axial pump is at least partially located in a patient's heart, obtain a set of motor speed measurements corresponding to rotational speeds of the motor during the period of time, and predict, using a trained machine learning model, an intra-aortic pressure of the patient based on the sets of intra-aortic pressure and motor speed measurements. The display is configured to display the predicted intra-aortic pressure of the patient.

In some implementations, the display is configured to simultaneously display the predicted intra-aortic pressure of the patient with a current intra-aortic pressure of the patient and a current speed setting of the motor. In some implementations, the display is further configured to display an alert when the predicted intra-aortic pressure of the patient is less than a current intra-aortic pressure of the patient by more than a predetermined amount. In some implementations, the display is configured to display the predicted intra-aortic pressure of the patient as part of a graph.

Yet another aspect of the present disclosure relates to a method for treating a patient with a transvalvular micro-axial heart pump received into the patient's body. The method includes: inserting a transvalvular micro-axial heart pump into the body of a patient, obtaining a set of intra-aortic pressure measurements corresponding to pressure values measured by a pressure sensor located on the transvalvular micro-axial heart pump during a period of time when the transvalvular micro-axial pump is at least partially located in the patient's heart, obtaining a set of motor speed measurements corresponding to rotational speeds of the motor during the period of time, predicting, using a trained machine learning model, an intra-aortic pressure of the patient based on the sets of intra-aortic pressure and motor speed measurements, and automatically adjusting a speed setting of the motor based on the predicted intra-aortic pressure of the patient.

In some implementations, the method further includes obtaining a set of current measurements corresponding to an energy intake of the motor during the period of time, and the prediction is further based on the set of current measurements.

In some implementations, the transvalvular micro-axial heart pump further includes a tube, an inlet area having one or more openings through which blood may be drawn into the tube by the motor, and an outlet area having one or more openings through which blood may be expelled from the tube by the motor, and the pressure sensor is coupled to the outlet area. In some implementations, the transvalvular micro-axial heart pump further includes an additional pressure sensor coupled to the inlet area, the method further includes obtaining a set of left ventricular pressure measurements corresponding to pressure values measured by the additional pressure sensor during the period of time, and the prediction is further based on the set of left ventricular pressure measurements.

In some implementations, the method further includes adjusting an amount of a medication provided to the patient based on the predicted intra-aortic pressure. In some implementations, the method further includes decreasing the motor speed if the intra-aortic pressure is predicted to increase. In some implementations, the method further includes increasing the motor speed if the intra-aortic pressure is predicted to decrease.

BRIEF DESCRIPTION OF DRAWINGS

FIG. 2(e) illustrates information that may be displayed on a home screen.

FIG. 2(h) illustrates information that may be displayed on a placement screen.

DETAILED DESCRIPTION

Figure 1B:
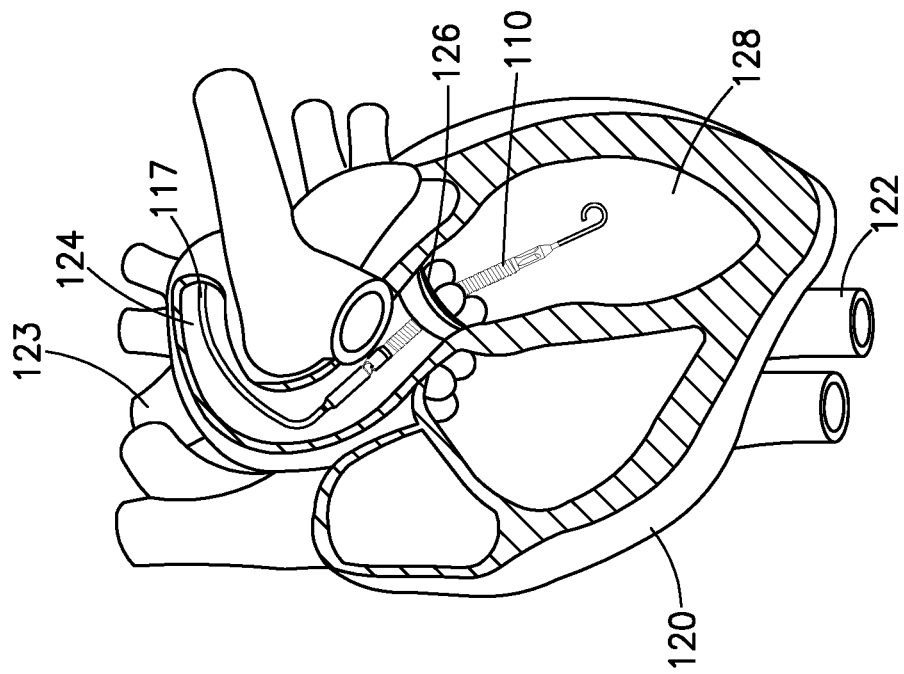
FIG. 1(b) illustrates the transvalvular micro-axial heart pump of FIG. 1(a) positioned within the heart of a patient.

Implementations of the present disclosure are described in detail with reference to the drawing figures wherein like reference numerals identify similar or identical elements. It is to be understood that the disclosed implementations are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Efforts have been made to predict the peripheral blood pressure of patients with various machine learning models and statistical methods. See, e.g., Abbasi et al., *Long-term Prediction of Blood Pressure Time Series Using Multiple Fuzzy Functions*, 21st Iranian Conference on Biomedical Engineering, ICBME, 2014; Peng et al., *Long-term Blood Pressure Prediction with Deep Recurrent Neural Networks*, arXiv:1705.04524v3, 2018.

Efforts have been made to predict whether patients are likely to experience an acute hypotensive episode (AHE) with various machine learning models and statistical methods. See, e.g., Henriques & Rocha, *Prediction of Acute Hypotensive Episodes Using Neural Network Multi-models*, Computers in Cardiology 36:549552, 2009; Moody & Lehman, *Predicting Acute Hypotensive Episodes: The 10th Annual PhysioNet/Computers in Cardiology Challenge*, Comput. Cardiol., 36(5445351): 541-544, 2009; Johnson et al., *MIMIC-III, a freely accessible critical care database*, Scientific Data, DOI: 10.1038/sdata.2016.35, 2016; Hatib et al., *Machine-learning Algorithm to Predict Hypotension Based on High-Fidelity Arterial Pressure Waveform Analysis*, Anesthesiology, 129(4):663-674, 2018.

Efforts have been made to predict acute decompensated heart failure (ADHF) with various machine learning models and statistical methods. See, e.g., Kenney et al., *Early Detection of Heart Failure Using Electronic Health Records*, Circ. Cardiovasc. Qual. Outcomes, 9:649-658, 2016; Deo & Nallamothu, Learning About Machine Learning: *The Promise and Pitfalls of Big Data and the Electronic Health Record*, Circ. Cardiovasc. Qual. Outcomes, 9:618-620, 2016; Passantino et al., *Predicting mortality in patients with acute heart failure: Role of risk scores*, World J. Cardiol., 7(12): 902911, 2015; Thorvaldsen et al., *Predicting Risk in Patients Hospitalized for Acute Decompensated Heart Failure and Preserved Ejection Fraction*, Circ. Heart Fail., 10:e003992, 2017.

However, none of the studies cited above describe systems or methods for predicting an intra-aortic pressure of a patient receiving hemodynamic support. Some of the cited studies describe systems or methods for predicting a peripheral blood pressure of a patient. However, peripheral blood pressure provides an indirect indication of a patient's cardiac function, whereas an intra-aortic pressure provides a direct indication of a patient's cardiac function. Peripheral blood pressure may be obtained using, for example, a blood pressure cuff wrapped around an extremity of a patient (e.g., an arm cuff or a wrist cuff), whereas an intra-aortic pressure may be obtained using, for example, a transvalvular micro-axial heart pump. As a result, a peripheral blood pressure is less informative of a patient's condition than an intra-aortic pressure.

Additionally, some of these approaches described in the studies cited above are not practical, at least from a clinical point of view, because they require an extensive number of input variables. Moreover, some of the variables used in the studies cited above are not easily measurable. Furthermore, some of the models proposed in the studies cited above are only suitable for evaluating long-term mortality. They cannot help physicians with real-time early detection of diseases, such as ADHF.

Patients with severe multi-vessel coronary artery disease (CAD), unprotected left main coronary artery stenosis, last remaining patent vessel, and/or severely reduced left ventricular (LV) ejection fraction (EF) are often turned down from cardiac surgery and are increasingly referred for high-risk percutaneous coronary intervention (HR-PCI). Transvalvular micro-axial heart pumps, such as the Impella 5.0® from Abiomed, Inc., Danvers, MA, shown in FIG. 1(a), are increasingly used during HR-PCI to prevent hemodynamic instability and improve clinical outcomes. See, e.g., Russo et al., *Hemodynamics and its predictors during transvalvular-micro-axial-heart-pump-protected PCI in high risk patients with reduced ejection fraction*, Int. J. Cardiol. 274:221-225, 2019; Dixon et al., *A prospective feasibility trial investigating the use of the transvalvular micro-axial heart pump system in patients undergoing high-risk percutaneous coronary intervention (The Transvalvular Micro-axial Heart Pump Trial): initial U.S. experience*, JACC Cardiovasc.

Interv. 2 (2) 91-96, 2009; O'Neill et al., *A prospective, randomized clinical trial of hemodynamic support with transvalvular micro-axial heart pump versus intra-aortic balloon pump in patients undergoing high-risk percutaneous coronary intervention: the transvalvular micro-axial heart pump study*, Circulation 126 (14) 1717-1727, 2012.

A transvalvular micro-axial heart pump is a percutaneous, catheter-based device that provides hemodynamic support to the heart of a patient. As shown in FIG. 1(a), a transvalvular micro-axial heart pump 110 may include a pigtail 111, an inlet area 112, a cannula 113, a pressure sensor 114, an outlet area 115, a motor housing 116, and/or a catheter tube 117. Pigtail 111 may assist with stabilizing transvalvular micro-axial heart pump 110 in the heart of a patient. During operation, blood may be drawn into one or more openings of inlet area 112, channeled through canula 113, and expelled through one or more openings of outlet area 115 by a motor (not shown) disposed in motor housing 116. In some implementations, pressure sensor 114 may include a flexible membrane that is integrated into cannula 113. One side of pressure sensor 114 may be exposed to the blood pressure on the outside of cannula 113, and the other side may be exposed to the pressure of the blood inside of cannula 113. In some such implementations, pressure sensor 114 may generate an electrical signal proportional to the difference between the pressure outside cannula 113 and the pressure inside cannula 113. In some implementations, a pressure difference measured by pressure sensor 114 may be used to position transvalvular micro-axial heart pump 110 within the heart of a patient. In some implementations, pressure sensor 114 is an optical pressure sensor. Catheter tube 117 may provide one or more fluidic and/or electrical connections between transvalvular micro-axial heart pump 110 and more or more other devices of a ventricular support system.

Figure 1A:
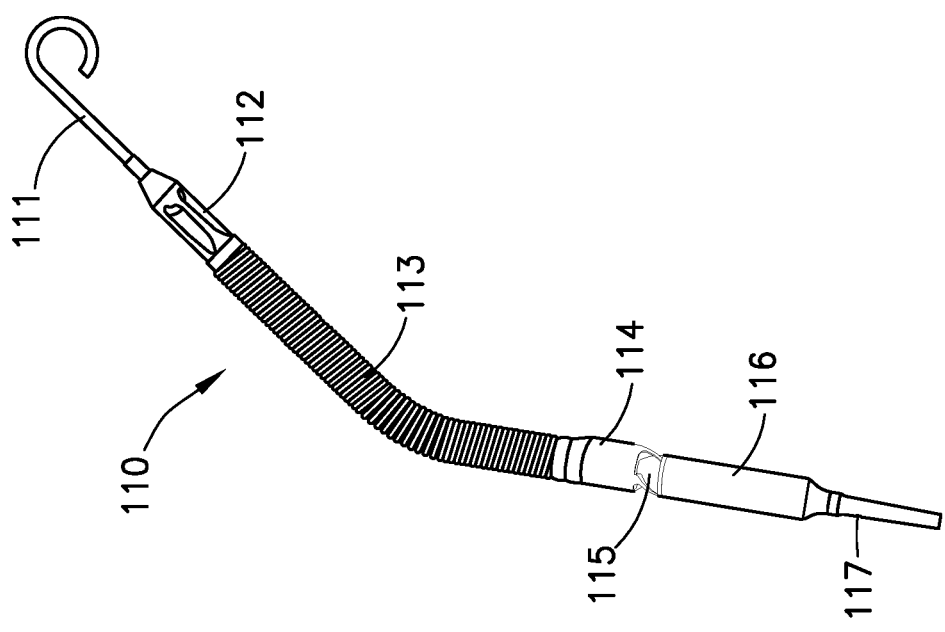
FIG. 1(a) illustrates a transvalvular micro-axial heart pump.

As shown in FIG. 1(b), transvalvular micro-axial heart pump 110 may be positioned in a patient's heart 120. As shown, transvalvular micro-axial heart pump 110 may, for example, be inserted percutaneously via the femoral artery 122 into the ascending aorta 124, across the aortic valve 126, and into the left ventricle 128. In other implementations, a transvalvular micro-axial heart pump may, for example, be inserted percutaneously via the axillary artery 123 into the ascending aorta 124, across the aortic valve 126, and into the left ventricle 128. In other implementations, a transvalvular micro-axial heart pump may, for example, be inserted directly into the ascending aorta 124, across the aortic valve 126, and into the left ventricle 128. During operation, transvalvular micro-axial heart pump 110 entrains blood from the left ventricle 128 and expels blood into the ascending aorta 124. As a result, transvalvular micro-axial heart pump 110 performs some of the work normally done by the patient's heart 120. The hemodynamic effects of transvalvular micro-axial heart pumps include an increase in cardiac output, improvement in coronary blood flow resulting in a decrease in LV end-diastolic pressure, pulmonary capillary wedge pressure, myocardial workload, and oxygen consumption. See, e.g., Burkhoff & Naidu, *The science behind percutaneous hemodynamic support: a review and comparison of support strategies*, Catheter Cardiovasc. Interv. 80:816-29, 2012.

Figure 1C:
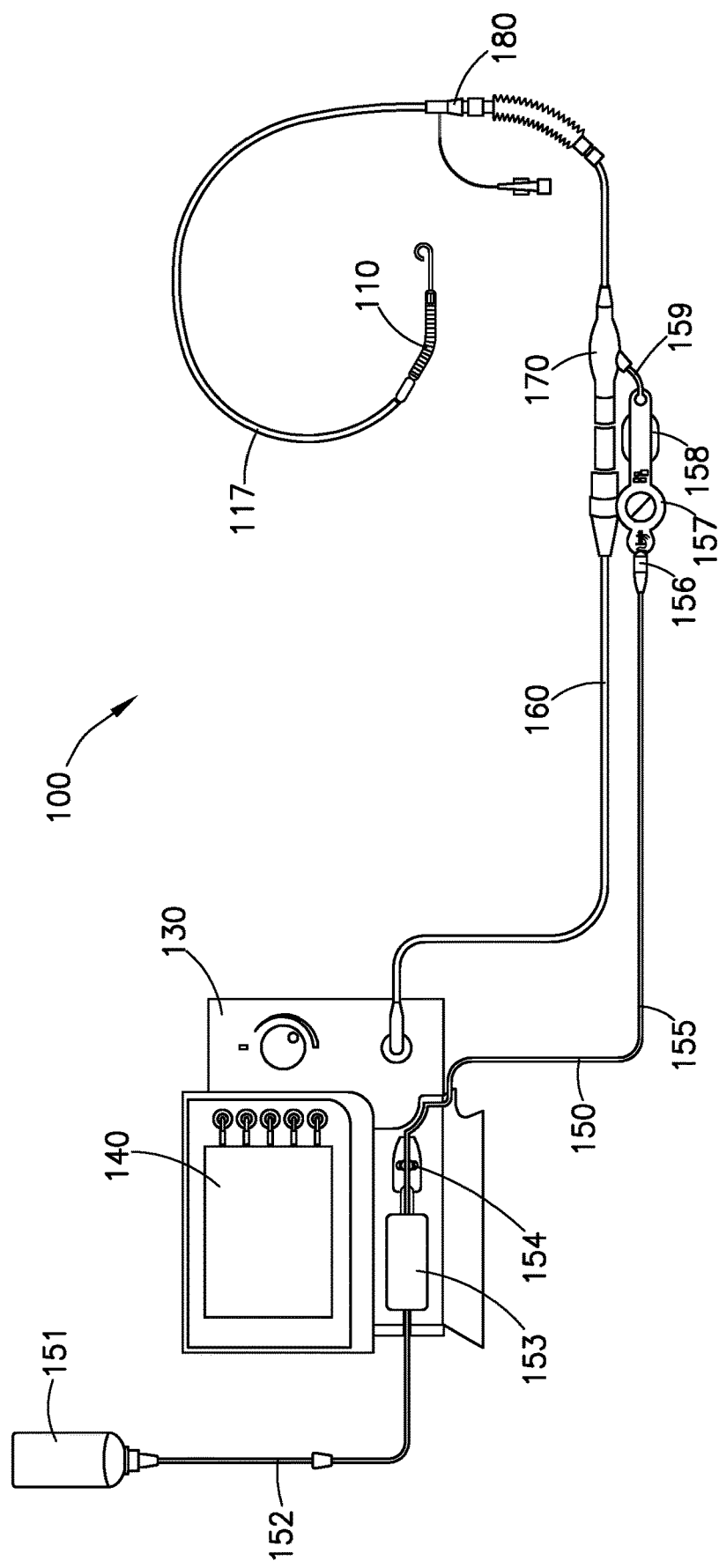
FIG. 1(c) illustrates a ventricular support system.

As shown in FIG. 1(c), transvalvular micro-axial heart pump 110 may be incorporated into a ventricular support system 100. Ventricular support system 100 also includes a controller 130 (e.g., an Automated Impella Controller® from Abiomed, Inc., Danvers, Mass.), a display 140, a purge subsystem 150, a connector cable 160, a plug 170, and a repositioning unit 180. As shown, controller 130 includes display 140. Controller 130 monitors and controls transvalvular micro-axial heart pump 110. During operation, purge subsystem 150 delivers a purge fluid to transvalvular micro-axial heart pump 110 through catheter tube 117 to prevent blood from entering the motor (not shown) within motor housing 116. In some implementations, the purge fluid is a dextrose solution (e.g., 5% dextrose in water with 25 or 50 IU/mL of heparin). Connector cable 160 provides an electrical connection between transvalvular micro-axial heart pump 110 and controller 130. Plug 170 connects catheter tube 117, purge subsystem 150, and connector cable 160. In some implementations, plug 170 includes a memory for storing operating parameters in case the patient needs to be transferred to another controller. Repositioning unit 180 may be used to reposition transvalvular micro-axial heart pump 110.

As shown, purge subsystem 150 includes a container 151, a supply line 152, a purge cassette 153, a purge disc 154, purge tubing 155, a check valve 156, a pressure reservoir 157, an infusion filter 158, and a sidearm 159. Container 151 may, for example, be a bag or a bottle. A purge fluid is stored in container 151. Supply line 152 provides a fluidic connection between container 151 and purge cassette 153. Purge cassette 153 may control how the purge fluid in container 151 is delivered to transvalvular micro-axial heart pump 110. For example, purge cassette 153 may include one or more valves for controlling a pressure and/or flow rate of the purge fluid. Purge disc 154 includes one or more pressure and/or flow sensors for measuring a pressure and/or flow rate of the purge fluid. As shown, controller 130 includes purge cassette 153 and purge disc 154. Purge tubing 155 provides a fluidic connection between purge disc 154 and check valve 156. Pressure reservoir 157 provides additional filling volume during a purge fluid change. In some implementations, pressure reservoir 157 includes a flexible rubber diaphragm that provides the additional filling volume by means of an expansion chamber. Infusion filter 158 helps prevent bacterial contamination and air from entering catheter tube 117. Sidearm 159 provides a fluidic connection between infusion filter 158 and plug 170.

During operation, controller 130 receives measurements from pressure sensor 114 and purge disc 154 and controls the motor (not shown) within motor housing 116 and purge cassette 153. As noted above, controller 130 controls and measures a pressure and/or flow rate of a purge fluid via purge cassette 153 and purge disc 154. During operation, after exiting purge subsystem 150 through sidearm 159, the purge fluid is channeled through purge lumens (not shown) within catheter tube 117 and plug 170. Sensor cables (not shown) within catheter tube 117, connector cable 160, and plug 170 provide an electrical connection between pressure sensor 114 and controller 130. Motor cables (not shown) within catheter tube 117, connector cable 160, and plug 170 provide an electrical connection between the motor within motor housing 116 and controller 130. During operation, controller 130 receives measurements from pressure sensor 114 through the sensor cables and controls the electrical power delivered to the motor within motor housing 116 through the motor cables. By controlling the power delivered to the motor within motor housing 116, controller 130 can control the speed of the motor within motor housing 116.

Various modifications can be made to ventricular support system 100 and one or more of its components. For example, as detailed in Abiomed, *Impella® Ventricular Support Systems for Use During Cardiogenic Shock and High-Risk PCI: Instructions for Use and Clinical Reference Manual*, Document No. 0042-9028 rG (Apr. 2020), which is incorporated herein by reference, ventricular support system 100 can be modified to accommodate other types of transvalvular micro-axial heart pumps, such as the Impella 2.5®, Impella LD®, and Impella CP® catheters. As another example, one or more sensors may be added to transvalvular micro-axial heart pump 100. For example, as described in U.S. patent application Ser. No. 16/353,132, which was filed on Mar. 14, 2019 and is entitled "Blood Flow Rate Measurement System," and which is incorporated herein by reference, a signal generator may be added to transvalvular micro-axial heart pump 100 to generate a signal indicative of the rotational speed of the motor within motor housing 116. As another example, a second pressure sensor may be added to transvalvular micro-axial heart pump 100 near inlet area 112 that is configured to measure a left ventricular blood pressure. In such implementations, additional sensor cables may be disposed within catheter tube 117, connector cable 160, and plug 170 to provide an electrical connection between the one or more additional sensors and controller 130. As yet another example, one or more components of ventricular support system 100 may be separated. For example, display 140 may be incorporated into another device in communication with controller 130 (e.g., wirelessly or through one or more electrical cables).

Figure 2A:
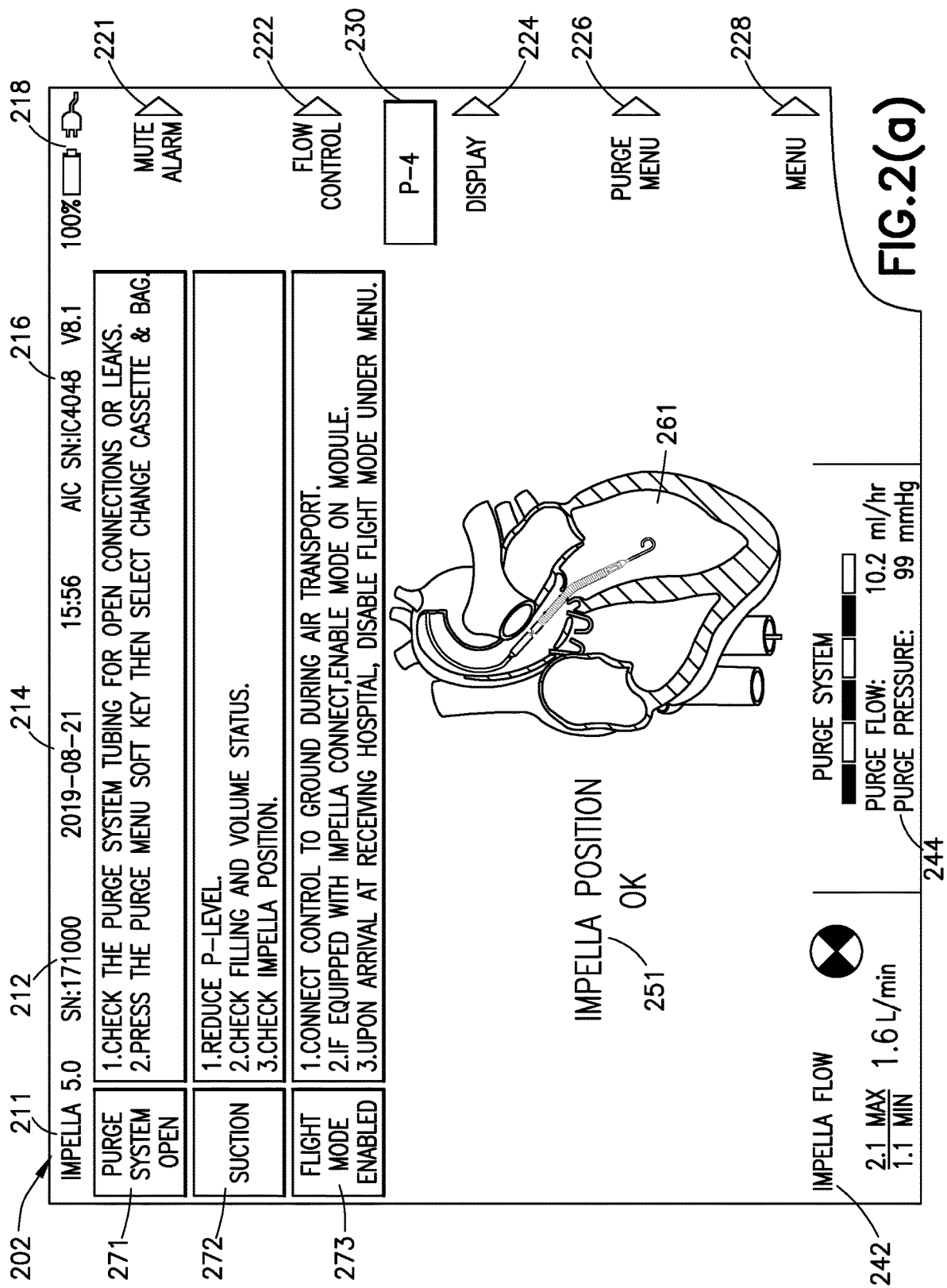
FIG. 2(a) illustrates information that may be displayed on a home screen.

FIGS. 2(a)-(h) illustrate different screens that may be displayed by display 140. For example, FIG. 2(a) illustrates a home screen 202 that includes a heart pump type 211 (e.g., "Impella 5.0"), a heart pump serial number 212 (e.g., "171000"), a date and time 214 (e.g., "2019-08-21 15:56"), a software version number 216 (e.g., "IC4048 V8.1"), a power source icon 218 (e.g., a battery indicator), button labels 221, 222, 224, 226, and 228 (e.g., "mute alarm," "flow control," "display," "purge menu," and "menu"), a present heart pump speed (performance) setting 230 (e.g., "P-4"), heart pump flow measurements 242, purge system measurements 244, a status indicator 251 (e.g., "Impella Position OK"), a diagram 261, and a notification area 270. Present heart pump speed (performance) setting 230 corresponds with a speed at which the motor within motor housing 116 is operating. For example, "P-4" may indicate that the motor within motor housing 116 is operating at approximately 22,000 rpm. Heart pump flow measurements 242 include a mean flow (e.g., "1.6 L/min"), a minimum flow (e.g., "1.1 L/min"), and a maximum flow (e.g., "2.1 L/min") of blood through transvalvular micro-axial heart pump 100. Heart pump flow measurements 242 may be derived from measurements obtained by pressure sensor 114 and/or an energy intake of the motor within motor housing 116. Purge system measurements 244 include a current flow (e.g., "10.2 ml/hr") and a current pressure (e.g., "99 mmHg") of purge fluid through purge subsystem 150. Purge system measurements 244 may be derived from measurements obtained by purge disc 154. Diagram 161 illustrates how transvalvular micro-axial heart pump 110 should be positioned in a patient's heart. In FIG. 2(a), notification area 270 includes notifications 271, 272, and 273.

Each of notifications 271, 272, and 273 includes a header and a set of instructions. For example, notification 271 includes the header "Purge System Open" and instructions to "1. Check the purge system tubing for open connections or leaks" and "2. Press the Purge Menu soft key then select Change Cassette & Bag." Notification 272 includes the header "Suction" and instructions to "1. Reduce P-Level," "2. Check filling and volume status," and "3. Check Impella position." Notification 273 include the header "Flight Mode Enabled" and instructions to "1. Connect controller to ground during air transport," "2. If equipped with Impella Connect, enable Flight Mode on module," and "3. Upon arrival at receiving hospital, disable Flight Mode under MENU." In other implementations, notifications displayed in notification area 270 may be structure differently. For example, the header and instructions may be contained in a single box, as opposed to two different boxes. As another example, the notifications may not include a header. As yet another example, the instructions may be replaced with a different type of information, such as an explanatory statement. For example, a notification may serve as an alert and include a statement describing the cause of the alert.

Figure 2B:
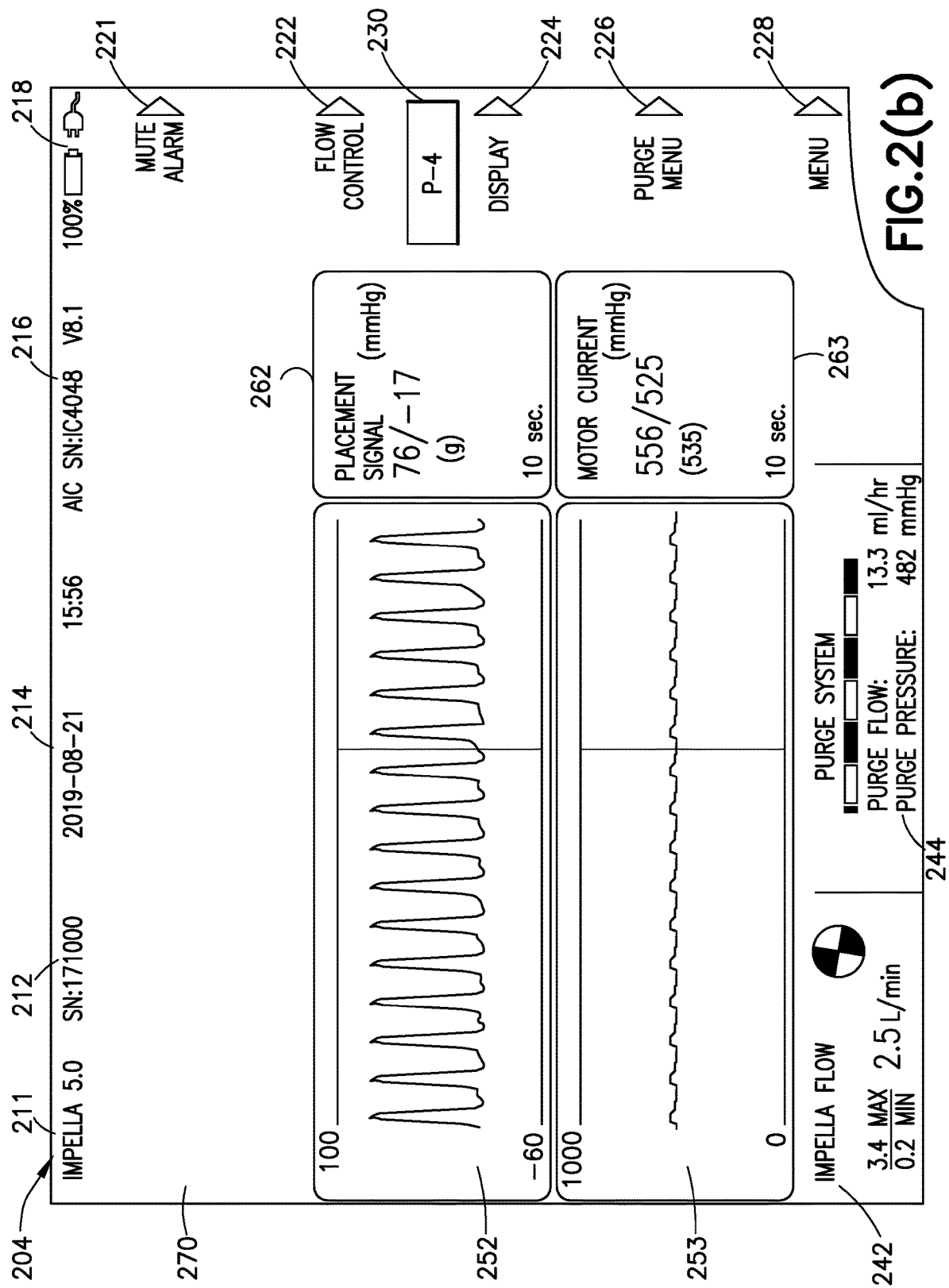
FIG. 2(b) illustrates information that may be displayed on a placement screen.
Figure 2C:
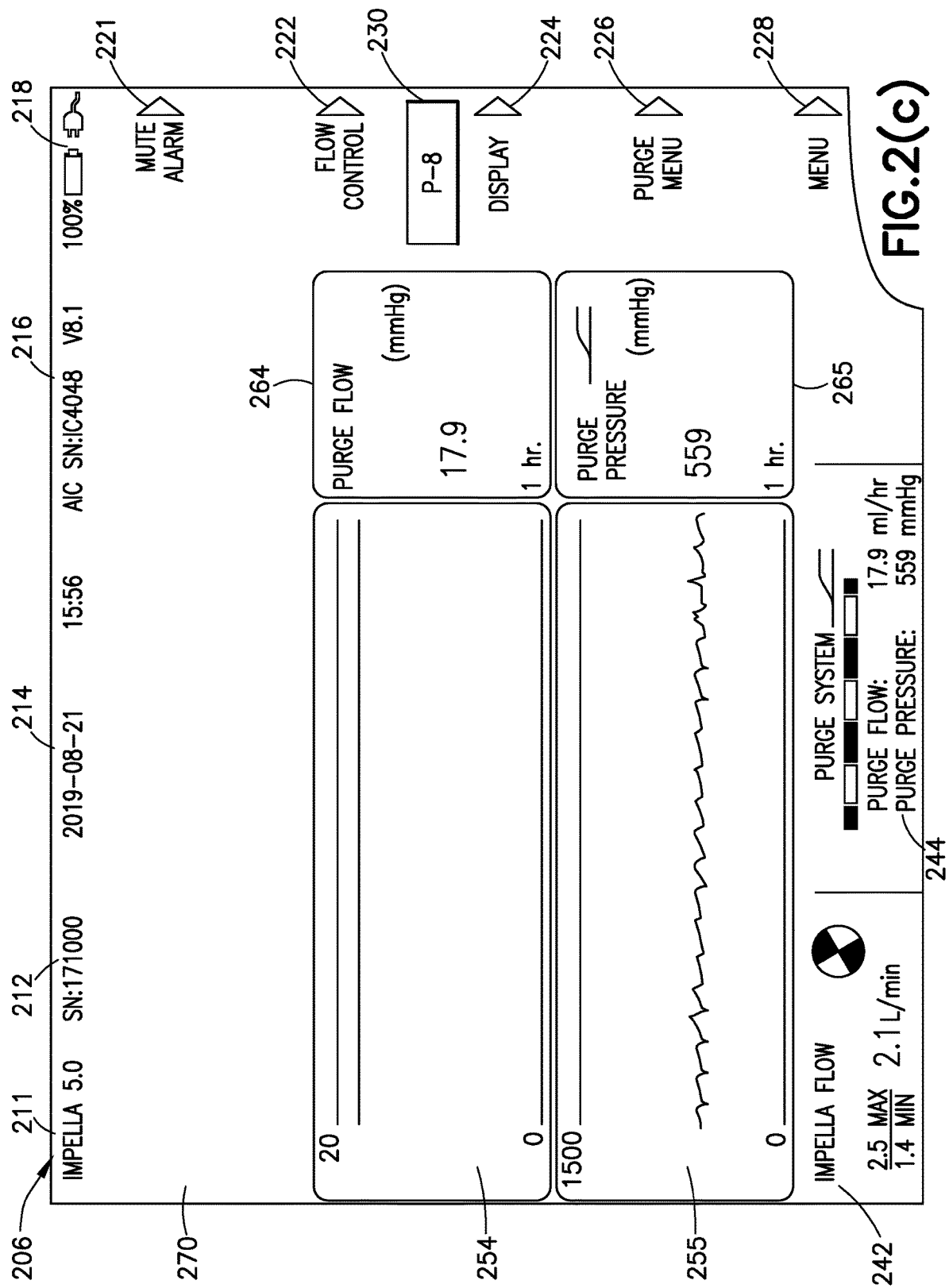
FIG. 2(c) illustrates information that may be displayed on a purge screen.
Figure 2D:
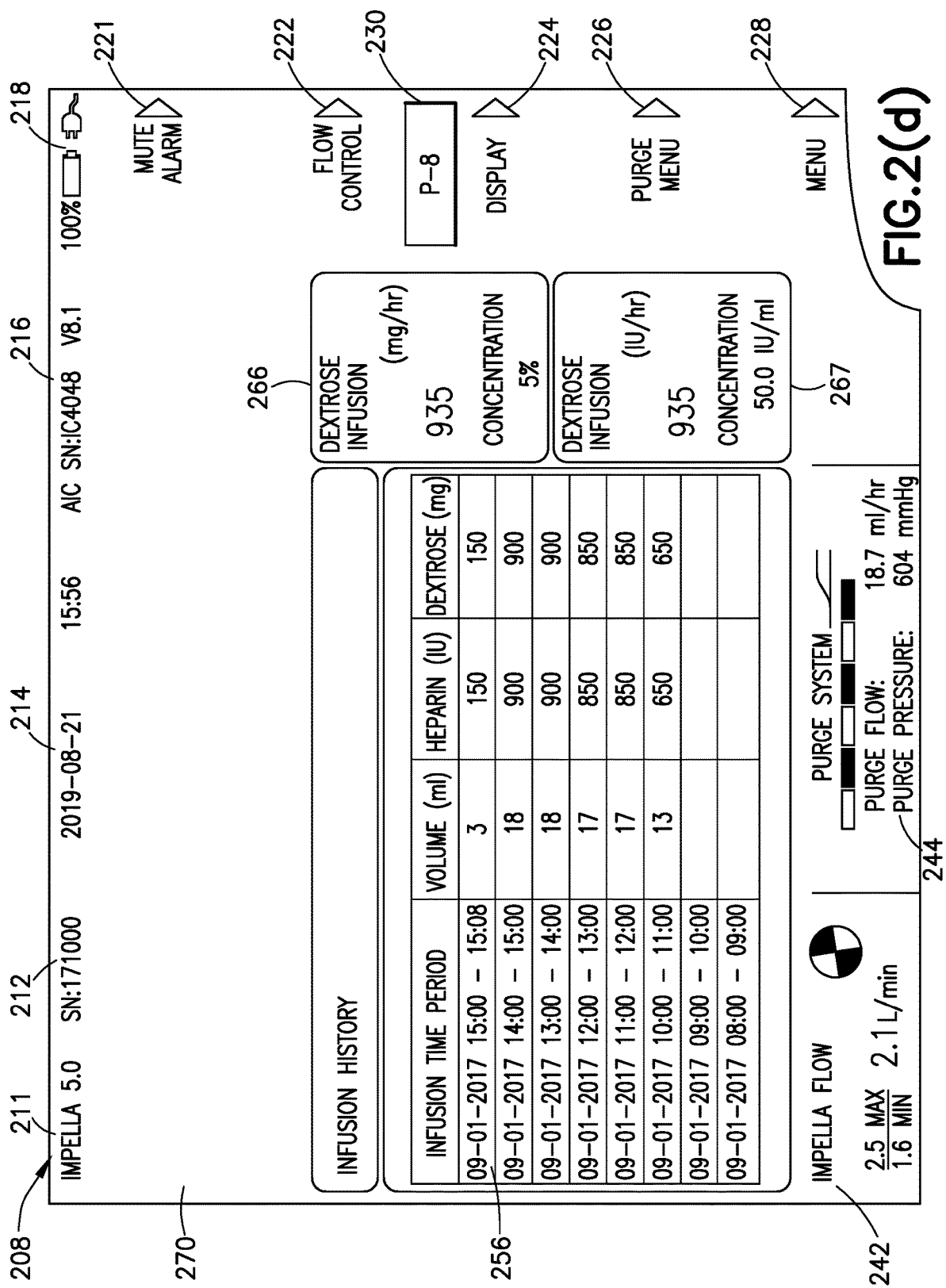
FIG. 2(d) illustrates information that may be displayed on an infusion history screen.
Figure 2F:
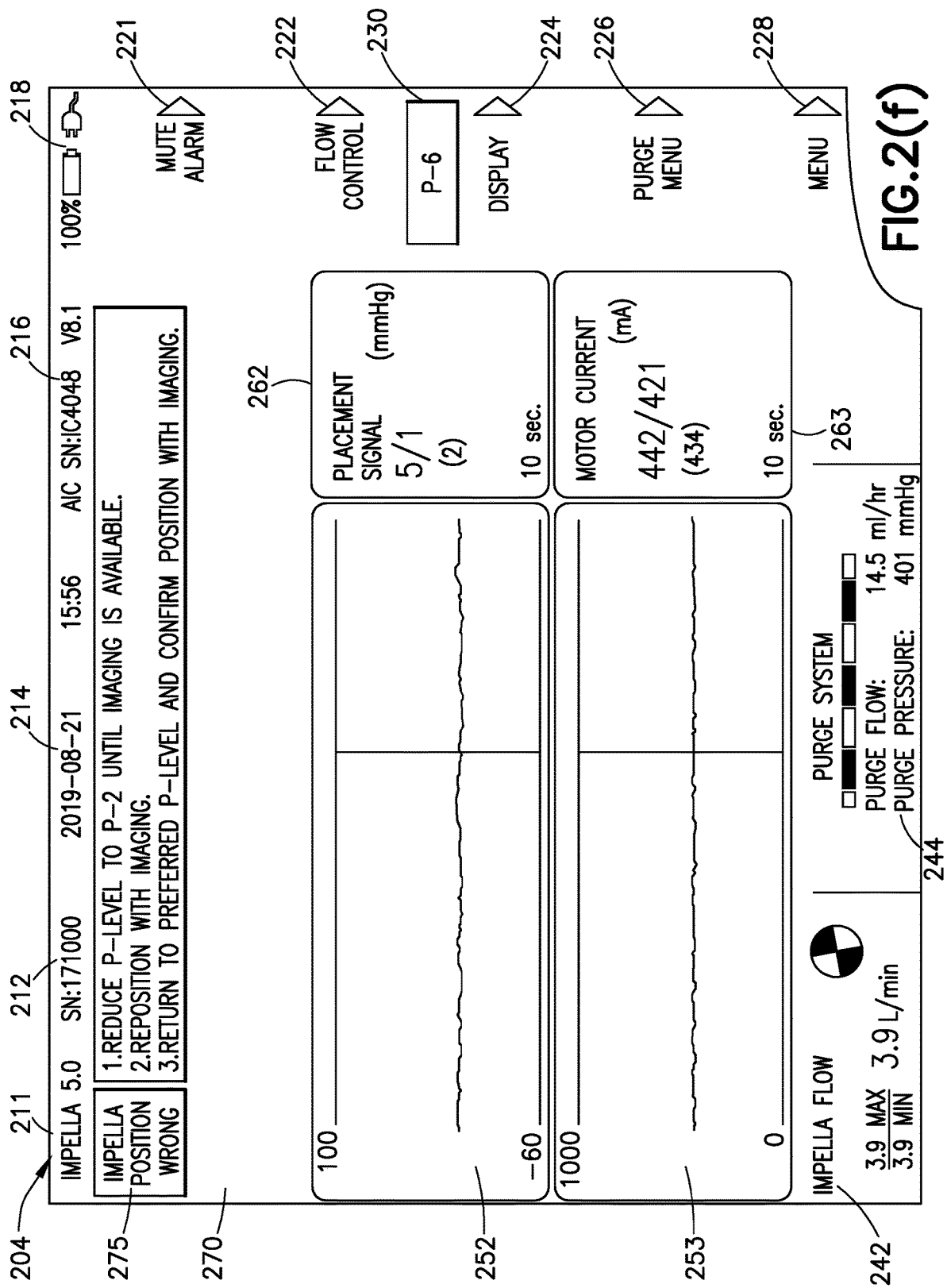
FIG. 2(f) illustrates information that may be displayed on a placement screen.
Figure 2G:
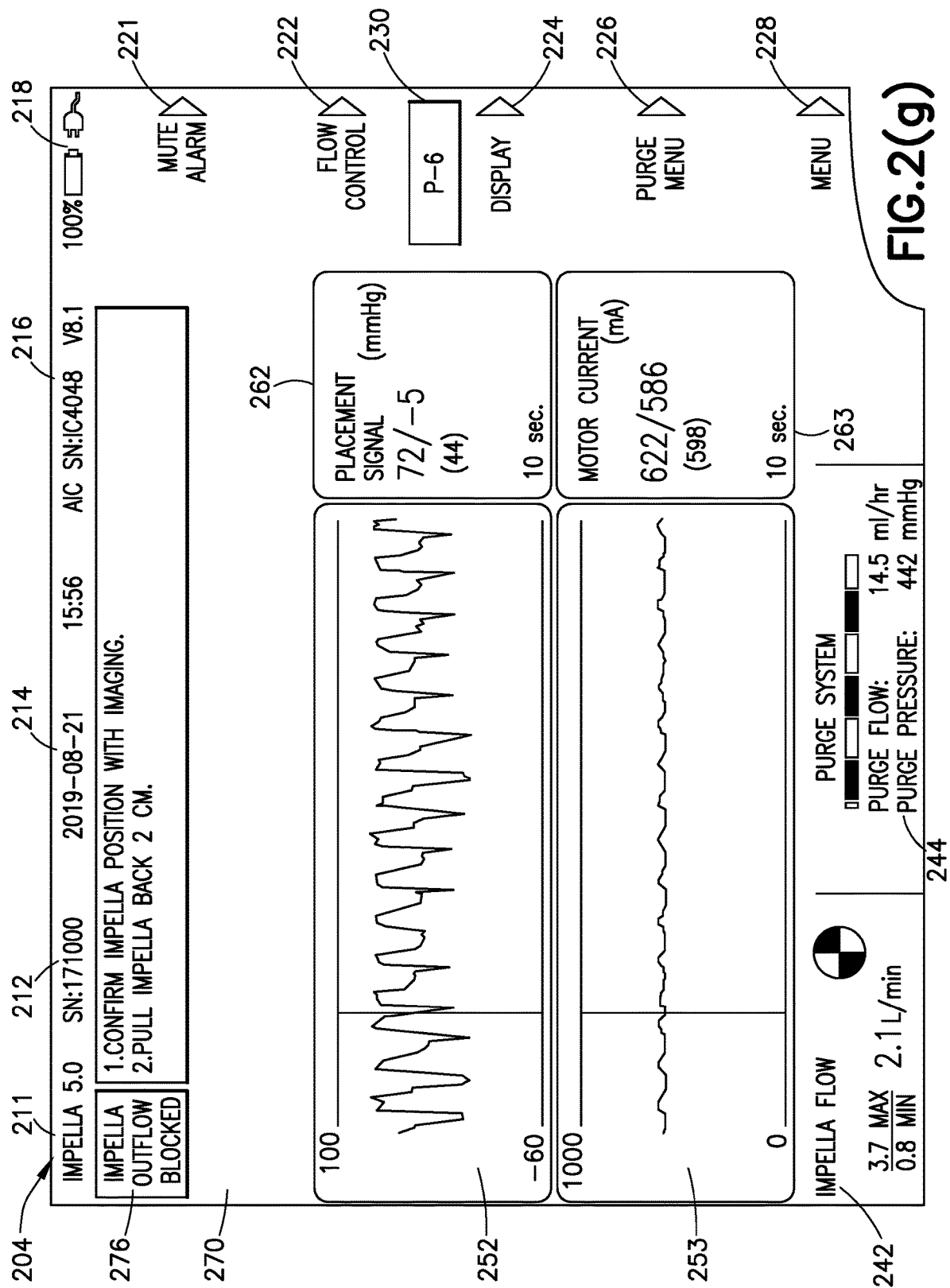
FIG. 2(g) illustrates information that may be displayed on a placement screen.

FIGS. 2(b)-(d) illustrate a placement screen 204, a purge screen 206, and an infusion history screen 208, respectively. A user may switch between these screens using buttons positioned alongside button labels 221, 222, 224, 226, and 228. In other implementations, different user input devices may be used. For example, in some implementations, display 140 may be a touchscreen and a user may switch between screens by tapping button labels 221, 222, 224, 226, and 228. As another example, in some implementations, a user may use a separate input device, such as a mouse or a keyboard, to switch between screens.

With the exception of status indicator 251, diagram 261, and notifications 271, 272, and 273, all of the data fields from home screen 202 are included in placement screen 204, purge screen 206, and infusion history screen 208. In other implementations, additional data fields may be added or removed from these screens. For example, in some implementations, heart pump type 211 and heart pump serial number 212 may only appear on main screen 202.

Placement screen 204, purge screen 206, and infusion history screen 208 also include additional information. For example, as shown in FIG. 2(b), placement screen 204 includes a placement signal graph 252, placement signal measurements 262, a motor current graph 253, and motor current measurements 263. Placement signal graph 252 illustrates pressure values derived from measurements obtained by pressure sensor 114 over a period of time (e.g., "10 sec."). Placement signal measurements 262 include a mean pressure value (e.g., "9 mmHg"), a minimum pressure value (e.g., "−17 mmHg"), and a maximum pressure value (e.g., "76 mmHg") derived from measurements obtained by pressure sensor 114 over the period of time. Motor current graph 253 illustrates current values provided to the motor within motor housing 116 over a period of time (e.g., "10 sec."). Motor current measurements 263 include a mean current (e.g., "535 mA"), a minimum current (e.g., "525 mA"), and a maximum current (e.g., "556 mA") provided to the motor within motor housing 116 over the period of time. Collectively, placement signal graph 252, placement signal measurements 262, motor current graph 253, and motor current measurements 263 are useful for determining a position of transvalvular micro-axial heart pump 110 within the heart of a patient.

As shown in FIG. 2(c), purge screen 206 additionally includes a purge flow graph 254, purge flow measurements 264, a purge pressure graph 255, and purge pressure measurements 265. Purge flow graph 254 illustrates a flow rate of a purge fluid through purge subsystem 150 over a period of time (e.g., "1 hr."). Purge flow measurements 264 include a current flow rate of a purge fluid through purge subsystem 150 (e.g., "17.9 ml/hr"). Purge pressure graph 255 illustrates a pressure of a purge fluid in purge subsystem 150 over a period of time (e.g., "1 hr."). Purge pressure measurements 265 include a current pressure of a purge fluid in purge subsystem 150 (e.g., "559 mmHg"). Collectively, purge flow graph 254, purge flow measurements 264, purge pressure graph 255, and purge pressure measurements 265 can assist with patient management.

As shown in FIG. 2(d), infusion history screen 208 additionally includes an infusion history table 256, dextrose infusion measurements 266, and heparin infusion measurements 267. Infusion history table 256 provides a summary of the amount of purge fluid, heparin, and dextrose delivered to the patient over each of a plurality of time periods (e.g., "10:00-11:00," "11:00-12:00," "12:00-13:00," "13:00-14:00," "14:00-15:00," and "15:00-15:08"). Dextrose infusion measurements 266 include a current rate at which dextrose is being delivered to the patient (e.g., "935 mg/hr"). Heparin infusion measurements 267 include a current rate at which heparin is being delivered to the patient (e.g., "935 IU/hr"). Collectively, infusion history table 256, dextrose infusion measurements 266, and heparin infusion measurements 267 can also assist with patient management.

FIGS. 2(e)-(h) illustrate how different types of alerts may be presented to a user through display 140. For example, when a patient has poor native ventricular function and controller 130 cannot determine a position of transvalvular micro-axial heart pump 110 within the heart of the patient, home screen 202 may be updated in the manner shown FIG. 2(e). More specifically, status indicator 251 may be updated to state "Impella Position Unknown" and notification 274 may be added to notification area 270. As another example, when transvalvular micro-axial heart pump 110 is fully in the ventricle or the aorta of the patient, placement screen 204 may be updated in the manner shown FIG. 2(f). More specifically, notification 275 may be added to notification area 270. As yet another example, when outlet area 115 is positioned on or near the aortic valve of the patient, placement screen 204 may be updated in the manner shown FIG. 2(g). More specifically, notification 276 may be added to notification area 270. As yet another example, when pressure sensor 114 fails and controller 130 is unable to calculate heart pump flow measurements 242, placement screen 204 may be updated in the manner shown FIG. 2(h). More specifically, heart pump flow measurements 242 may be replaced with a table of estimated flows and corresponding MAPs and notification 277 may be added to notification area 270.

Figure 3:
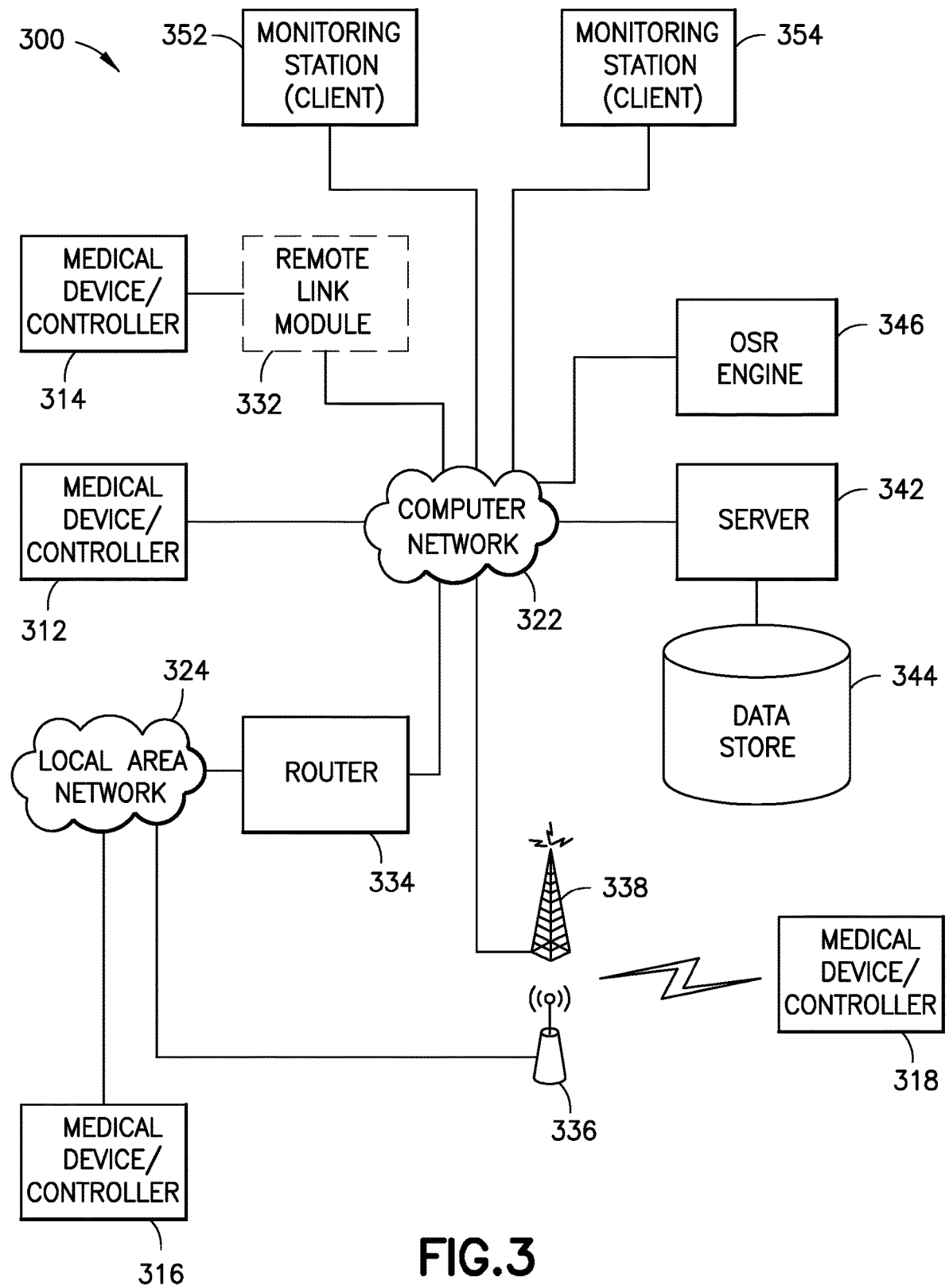
FIG. 3 illustrates a system for monitoring and/or controlling a plurality of medical devices, such as transvalvular micro-axial heart pumps.

FIG. 3 illustrates a system 300 for monitoring and/or controlling a plurality of medical device controllers, such as controller 130. System 300 may include medical device controllers 312, 314, 316, and 318, computer network 322, local area network (LAN) 324, remote link module 332, router 334, wireless access point 336, cell site 338, server 342, data store 344, OCR engine 346, and/or monitoring stations 352 and 354. Computer network 322 may include wired and/or wireless segments and/or networks. For example, computer network 322 may include wireless networks that conform to an IEEE 802.11x standard (e.g., wireless local area networks (WLANs), commonly referred to as "Wi-Fi"), represented by wireless access point 336, and/or cellular networks, represented by cell site 338. As another example, computer network 322 may include private and/or public networks, such as LAN 324, metropolitan area networks (MANs), and/or wide area networks (WANs), such as the Internet (not shown).

System 300 illustrates a few different ways in which medical device controllers can be connected to computer network 322. For example, medical device controller 312 is directly connected to computer network 322. As another example, medical device controller 314 is optionally connected to computer network 322 through remote link module 332. As yet another example, medical device controller 316 is connected to computer network 322 through LAN 324 and router 334. As yet another example, medical device controller 318 is connected to computer network 322 through LAN 324, router 334, and wireless access point 336. Medical device controller 318 is also connected to computer network 322 through cell site 338. In other implementations, medical device controllers may be added and/or removed from system 300. Furthermore, multiple medical device controllers may be connected to computer network 322 in a similar manner. For example, a plurality of medical device controllers may be directly connected to computer network 322, much like medical device controller 312.

Server 342 may be configured to request status information from medical device controllers 312, 314, 316, and 318 through computer network 322. In some implementations, server 342 requests the status information automatically and/or repeatedly. In some implementations, the status information includes an image of the contents of a screen displayed by a display associated with medical device controllers 312, 314, 316, and/or 318. For example, the status information may be similar to an image of any one of the screens illustrated in FIGS. 2(a)-(h). The image may be sent in one or more messages encoded as a video frame or a sequence of video frames. Furthermore, the video frame(s) may, for example, contain pixelated copies of the image. In some implementations, the status information includes information from one or more of the data fields displayed by a display associated with medical device controllers 312, 314, 316, and/or 318. For example, the status information may include information from one or more of the data fields similar to heart pump type 211, heart pump serial number 212, date and time 214, present heart pump speed (performance) setting 230, heart pump flow measurements 242, purge system measurements 244, status indicator 251, and/or notification area 270.

Server 342 may also be configured to process the received status information. For example, when server 342 receives an image of the contents of a screen displayed by a display associated with medical device controllers 312, 314, 316, and/or 318, server 342 may parse the images and extract textual information by optical character recognizing (OCR) portions of the image. In some implementations, the extracted textual information includes information from one or more of the data fields displayed by a display associated with medical device controllers 312, 314, 316, and/or 318. In some implementations, server 342 includes an OCR engine for parsing images and extracting textual information. In some implementations, server 342 communicates with an external OCR engine, such as OCR engine 346, for parsing images and extracting textual information.

Data store 344 may be configured to store unprocessed and/or processed status information. For example, data store 344 may store an image of the contents of a screen displayed by a display associated with medical device controllers 312, 314, 316, and/or 318 and/or textual information extracted from the image by server 342 and/or OCR engine 346. Data store 344 may also be configured to provide at least some of the unprocessed and/or processed status information to monitoring stations 352 and 354 upon request. Monitoring stations 352 and 354 may be, for example, a phone, tablet, and/or computer. In some implementations, monitoring stations 352 and 354 may use cloud-based technology to securely and remotely display at least some of the unprocessed and/or processed status information on associated displays. For example, monitoring stations 352 and 354 may use an online device management system, such as the Impella Connect® from Abiomed, Inc., Danvers, Mass., to securely and remotely display at least some of the unprocessed and/or processed status information.

In some implementations, server 342 and/or monitoring stations 352 and/or 354 may also be configured to remotely send commands to one or more medical device controllers within system 300 (e.g., medical device controllers 312, 314, 316, and/or 318). For example, if controller 130 is added to system 300, server 342 and/or monitoring stations 352 and/or 354 may be configured remotely adjust the power delivered to the motor within motor housing 116, the flow rate of a purge fluid through purge subsystem 150, and/or the pressure of a purge fluid in purge subsystem 150 by remotely sending a command to controller 130. In some implementations, one or more medical device controllers within system 300 (e.g., medical device controllers 312, 314, 316, and/or 318) may offload one or more computations to server 342 and/or monitoring stations 352 and/or 354. For example, if controller 130 is added to system 300, controller 130 may offload complex calculations (e.g., machine learning algorithms) to server 342 and/or monitoring stations 352 and/or 354. To reduce latency, controller 130 may also offload such calculations to another computing device on the same LAN (not shown).

Figure 4:
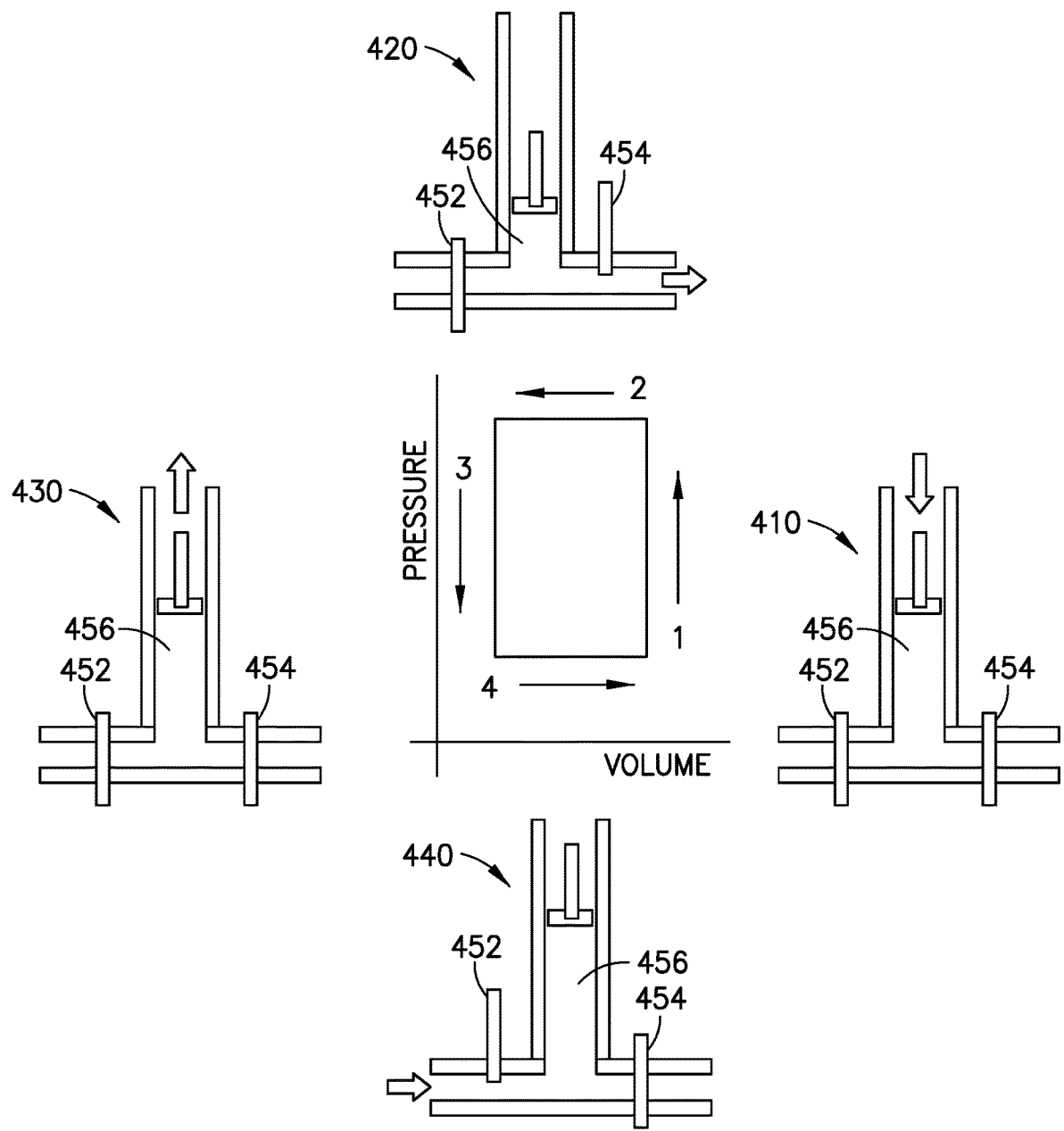
FIG. 4 illustrates the isovolumic relaxation phase, the ejection phase, the isovolumic relaxation phase, and the filling phase of a cardiac cycle.

As shown in FIG. 4, the cardiac cycle contains four phases: isovolumic contraction phase 410, ejection phase 420, isovolumic relaxation phase 430, and filling phase 440. During the cardiac cycle, the contraction and relaxation of the heart muscles in the heart chamber causes two valves, mitral valve 452 and aortic valve 454, to open and close due to pressure differences. During isovolumic contraction phase 410, mitral valve 452 and aortic valve 454 are closed and the pressure in chamber 456 increases until it is so high that aortic valve 454 opens. During ejection phase 420, mitral valve 452 is closed, aortic valve 454 is open, and blood flows out of chamber 456 into the aorta. During isovolumic relaxation phase 430, mitral valve 452 and aortic valve 454 are closed and pressure in chamber 456 decreases until it is so low that mitral valve 452 opens. During filling phase 440, mitral valve 452 is open, aortic valve 454 is closed, and blood flows into chamber 456. The first two phases are known as systole and the last two phases are known as diastole.

Figure 5:
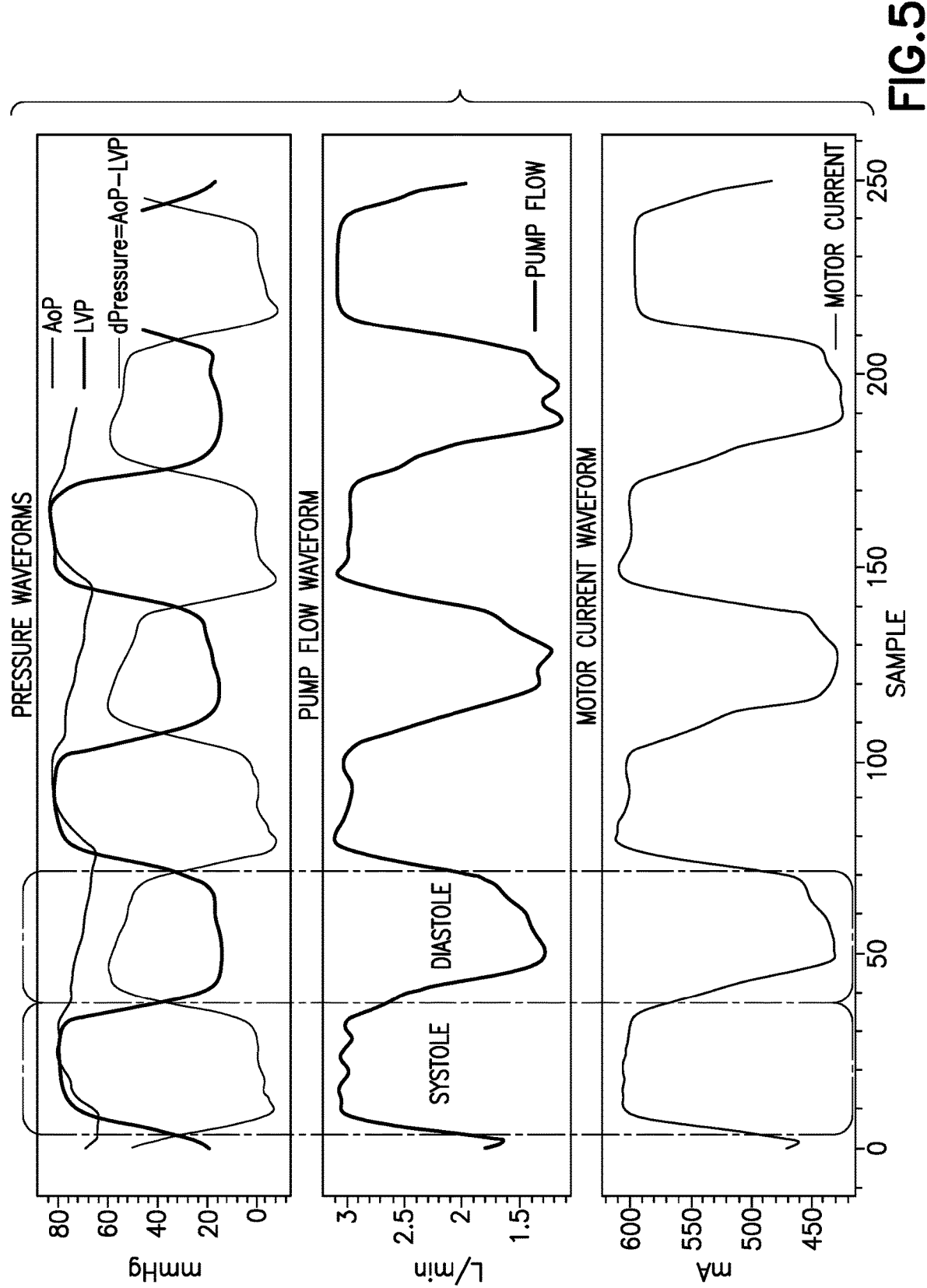
FIG. 5 illustrates the regular waveforms of Intra-Aortic Pressure (AoP), Left Ventricular Pressure (LVP), Differential Pressure (dP), Pump Flow, and Motor Current, as well as their relationships with systole and diastole.

FIG. 5 illustrates the regular waveforms of Intra-Aortic Pressure (AoP), Left Ventricular Pressure (LVP), Differential Pressure (dP), Pump Flow, and Motor Current, as well as their relationships with systole and diastole. The AoP waveform corresponds with the pressure in the ascending aorta of a patient (e.g., ascending aorta 124). The LVP waveform corresponds with the pressure in the left ventricle of the patient (e.g., left ventricle 128). The dP waveform corresponds with the pressure differential between the ascending aorta and left ventricle of the patient. The Pump Flow waveform corresponds with a rate at which blood is drawn into the ascending aorta from the left ventricle by a transvalvular micro-axial heart pump (e.g., transvalvular micro-axial heart pump 110). The Motor Current waveform corresponds with the current provided to a motor of the transvalvular micro-axial heart pump (e.g., the motor within motor housing 116).

Maintenance of a constant mean intra-aortic pressure (MAP) is vital to ensure adequate organ perfusion. See, e.g., Chemla et al., *Mean aortic pressure is the geometric mean of systolic and diastolic aortic pressure in resting humans*, Journal of Applied Physiology 99:6, 2278-2284, 2005. Studies show that increases in the duration of time spent below a MAP threshold of 65 mmHg are associated with worse patient outcomes, such as risk of mortality or organ dysfunction. See, e.g., Varpula et al., *Hemodynamic variables related to outcome in septic shock*, Intensive Care Med. 31:1066-1071, 2005; Dunser et al., Arterial blood pressure during early sepsis and outcome, Intensive Care Med. 35:1225-1233, 2009; Dunser et al., *Association of arterial blood pressure and vasopressor load with septic shock mortality: a post hoc analysis of a multicenter trial*, Crit. Care Lond. Engl. 13:R181, 2009. As shown in FIG. 5, physiologic waveforms obtained using catheter-based hemodynamic support devices, such as a transvalvular micro-axial heart pump, can be a rich source of hemodynamic information. However, forewarnings regarding a patient's status based on a forecasted time series of MAP using such devices is scarce.

Aspects of the present disclosure describe systems and methods for predicting an intra-aortic pressure of a patient receiving hemodynamic support from a transvalvular micro-axial heart pump. Advance warning of imminent changes in intra-aortic pressure (e.g., MAP), even if the warning comes only 5 to 15 minutes ahead, can aid in prompt management of a patient prior to a total hemodynamic collapse. For example, if a patient's intra-aortic pressure is predicted to increase or remain stable, then a clinician may initiate or continue a percutaneous coronary intervention (PCI) procedure. Similarly, if a patient's intra-aortic pressure is predicted to decrease, then a clinician may delay or terminate a PCI procedure. Generally, significant decreases in a patient's predicted intra-aortic pressure (e.g., decreases of at least 10 mmHg) indicate that the patient's condition is worsening. However, a sustained increase may also indicate that the patient's condition is deteriorating.

Forecasting stable trends in the intra-aortic pressure can also serve as a signal to wean the patient off the transvalvular micro-axial heart pump. Similarly, a projected intra-aortic pressure could be used to assign the level of support provided to the patient during the weaning process. For example, a clinician may adjust the pharmacological support provided to the patient based on a predicted intra-aortic pressure (e.g., by adjusting an amount of a medication, such as a vasopressor or an inotrope, provided to the patient). As another example, a motor speed setting (e.g., present heart pump speed (performance) setting 230) can be manually adjusted by a clinician and/or automatically adjusted by a connected medical device controller (e.g., controller 130) based on the projected intra-aortic pressure. For example, in some implementations, the medical device controller may be configured to wean a patient off support by automatically and gradually decreasing the motor speed setting over time. In such implementations, the medical device may, for example, temporarily increase the motor speed setting if the patient's condition is predicted to worsen (e.g., the patient's intra-aortic pressure is predicted to significantly decrease).

In some implementations, a display associated with a transvalvular micro-axial heart pump (e.g., display 140) may be configured to display a predicted intra-aortic pressure so that a clinician can react accordingly. For example, in relation to the screens illustrated in FIGS. 2(*a*)-(*h*), the predicted intra-aortic pressure may be displayed alongside heart pump flow measurements 242 and/or purge system measurements 244. As another example, any significant changes in intra-aortic pressure (e.g., +/−10 mmHg) may cause a notification to be displayed in notification area 270 or an update to status indicator 251. As yet another example, an intra-aortic pressure forecasting screen may be displayed that includes a graph of the predicted intra-aortic pressure over time, much like placement signal graph 252. As yet another example, a graph of the predicted intra-aortic pressure over time may be added to home screen 202, placement screen 204, purge screen 206, and/or infusion history screen 208 and/or replace a data field in one of those screens (e.g., placement signal graph 252, motor current graph 253, purge flow graph 254, and/or purge pressure graph 255).

As explained above, a transvalvular micro-axial heart pump not only provides hemodynamic support, thus aiding in native heart function recovery, but it is also equipped with, for example, one or more sensors (e.g., pressure sensor 114) to capture measurements at origin, instead of peripherally. Collectively, the measurements obtained from the one or more sensors of a transvalvular micro-axial heart pump and the operating characteristics of the motor of the transvalvular micro-axial heart pump (e.g., the motor within motor housing 116) can provide a rich set of data to which a machine learning algorithm can be applied to predict an intra-aortic pressure of a patient. For example, a machine learning algorithm can be applied to a set of features including intra-aortic pressure, motor current, motor speed, and/or a motor speed setting (e.g., P-0, P-1, P-2, P-3, P-4, P-5, etc. for an Impella Catheter from Abiomed, Inc., Danvers, Mass.). Intra-aortic pressure may be derived from measurements obtained by the pressure sensor of the transvalvular micro-axial heart pump. Motor current may be derived from an energy intake of the motor of the transvalvular micro-axial heart pump. Motor speed may be derived from measurements obtained by a signal generator of the transvalvular micro-axial heart pump. Motor speed may also be derived from a back electromotive force (EMF) of the motor of the transvalvular micro-axial heart pump. In some implementations, the motor of the transvalvular micro-axial heart pump includes three or more motor windings. In such implementations, the back EMF may be derived from, for example, a measured voltage across a motor winding disconnected from a power supply. In some implementations, the power supply may be in a connected medical device controller (e.g., controller 130).

A variety of different machine learning algorithms, such as Bayesian algorithms, clustering algorithms, decision tree algorithms, dimensionality reduction algorithms, instance-based algorithms, deep learning algorithms, regression algorithms, regularization algorithms, and rule-based machine learning algorithms, can be applied to measurements from a transvalvular micro-axial heart pump to predict an intra-aortic pressure of a patient. Some examples of deep learning algorithms include the Autoregressive Integrated Moving Average (ARIMA) models, Deep Neural Network (DNN) models, Recurrent Sequence to Sequence models, Recurrent Sequence to Sequence models with Attention, Transformer models, Temporal Convolutional Neural Network (TCN) models, and Convolutional Neural Pyramid models. In some implementations, these machine learning algorithms may be implemented by a medical device controller connected to the transvalvular micro-axial heart pump (e.g., controller 130). In other implementations, some or all of this processing may be offloaded to another device over a computer network (e.g., server 342).

The ARIMA model is a popular statistical method for time series forecasting. The components of the model are Autoregression (AR), Integrated, and Moving Average (MA). As a result, this model uses (a) the dependent relationship between an observation and some number of lagged observations, (b) the differencing of raw observations (subtracting an observation from an observation at the previous time step) in order to make the time series stationary, and (c) the dependency between an observation and a residual error from a moving average model applied to lagged observations. Additional information regarding the ARIMA model can be found in Hyndman & Athanasopoulos, *Forecasting: principles and practice,* 2nd edition, Chapter 8 ARIMA models, OTexts: Melbourne, Australia, OTexts.com/fpp2, 2018, which is incorporated herein by reference.

A feed-forward Deep Neural Network (DNN) may be formed by one input layer, multiple hidden layers, and one output layer. A DNN may be used in an autoregressive manner. In such implementations, a DNN may be built with a single unit in the output layer to perform one step ahead forecasting, and keep recursively feeding back the predictions for multiple steps ahead forecasting. Additional information regarding DNN models can be found in Schmidhuber, *Deep Learning in Neural Networks: An Overview*, arXiv:1404.7828v4, 2014, which is incorporated herein by reference.

Figure 6:
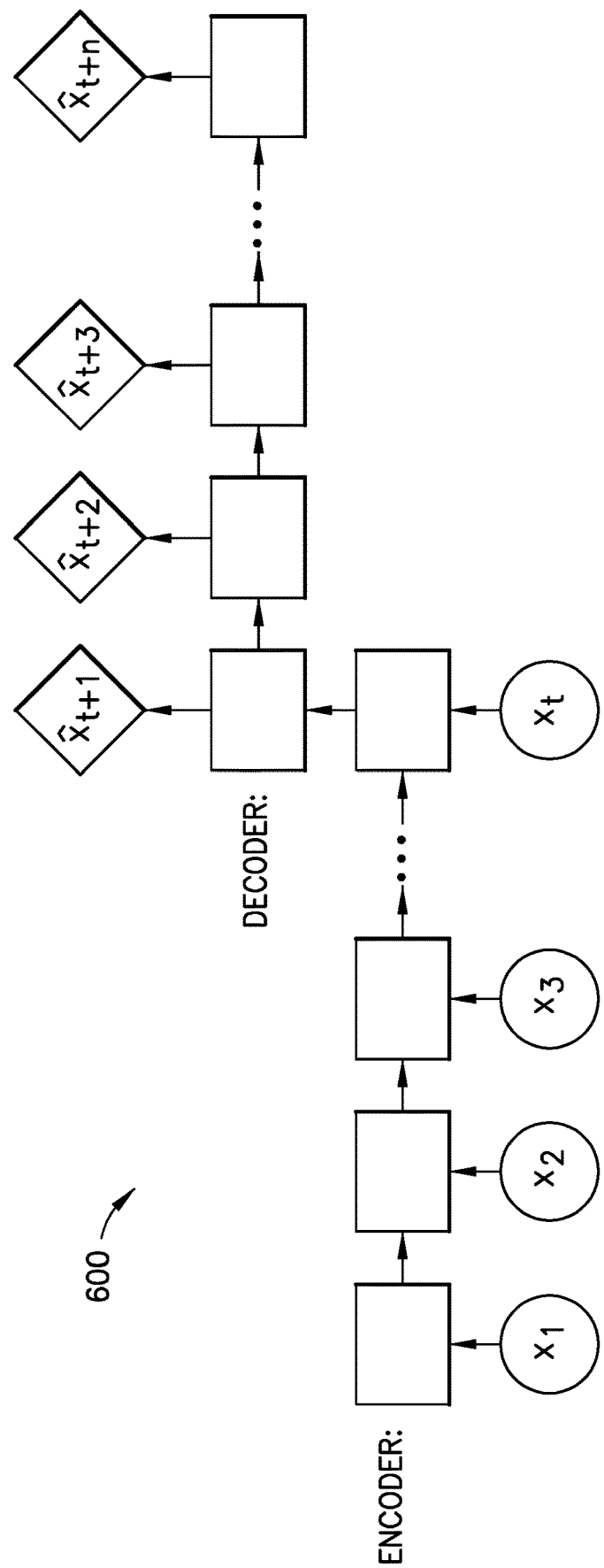
FIG. 6 illustrates the overall structure of a recurrent sequence to sequence model.

Recurrent Sequence to Sequence models map an input sequence to a fixed-sized vector using one encoder, and then map the vector to a target sequence with a decoder. Additional information regarding Recurrent Sequence to Sequence models can be found in Sutskever et al., *Sequence to Sequence Learning with Neural Networks*, NeurIPS 2014, which is incorporated herein by reference. Recurrent neural network (RNN) models may be used to retain the temporal information in the time series, as its hidden layers can memorize information processed through shared weights. For the encoder, a bidirectional RNN model may be used so that the model can process the data in both the forward and backward directions. In some implementations, two separate hidden layers may be used and then merged to the same output layer. For the decoder, an RNN model may be used to decode the target sequence from the hidden states. However, RNN models have trouble learning long-term dependencies due to vanishing gradients. Long Short-Term Memory (LSTM) Units can alleviate the vanishing gradients issue with a memory cell state. The overall structure 600 of a Recurrent Sequence to Sequence Model with LSTM units is illustrated in FIG. 6. Additional information regarding LSTMs can be found in Hochreiter & Schmidhuber, *Long Short-Term Memory*, Neural Computation, Volume 9 Issue 8, 1997, which is incorporated herein by reference. As used in the remainder of the present disclosure, a Recurrent Sequence to Sequence Models with LSTM units is simply referred to as an "LSTM."

Recurrent Sequence to Sequence models need to compress all necessary information of input into one fixed length vector from which to decode each output time step. As a result, it may be difficult for an encoder-decoder network to learn all useful information. Attention mechanisms may be applied to alleviate this problem. Attention mechanisms can learn local information by utilizing intermediate encoder states for the context vectors used by the decoder. Thus, attention mechanisms may be used, as opposed to functions, to overcome the disadvantage of fixed-length context vector by creating shortcuts between the context vector and the entire source input. Additional information regarding attention mechanisms can be found in Luong et al., *Effective Approaches to Attention-based Neural Machine Translation*, arXiv:1508.04025, 2015, which is incorporated herein by reference.

The Legendre Memory Unit (LMU) further addresses the issue of vanishing and exploding gradients commonly associated with training RNNs by using cell structure derived from first principles to project continuous-time signals onto d orthogonal dimensions. The LMU provides theoretical guarantees for learning long-range dependencies even as the discrete time-step, Δt, approaches zero. This enables the gradient to flow across the continuous history of internal feature representations. The LMU is a recent innovation that achieves state-of-the-art memory capacity while ensuring energy efficiency, making it especially suitable for the chaotic time-series prediction task in the medical domain. Additional information regarding the LMU can be found in Voelker et al., *Legendre Memory Units: Continuous-Time Representation in Recurrent Neural Networks*, NeurIPS 2019, which is incorporated herein by reference.

The Transformer model is a transduction model that relies entirely on self-attention (note that attention here is different from the one previously described) to compute representations of its input and output without using sequence-aligned RNN or convolutions. Both the encoding and the decoding components are stacks of identical layers, each of which is composed of two sublayers: one multi-head attention layer and one fully connected layer. The decoder has both those layers, but between them is an attention layer that helps the decoder focus on the output of the encoder stack. Instead of using a single scaled dot-product attention, the Transformer model projects the queries Q, keys K, and values V to an output as follows:

$$\text{Attention}(Q, K, V) = \text{softmax}\left(\frac{QK^T}{\sqrt{d_k}}V\right)$$

Figure 7:
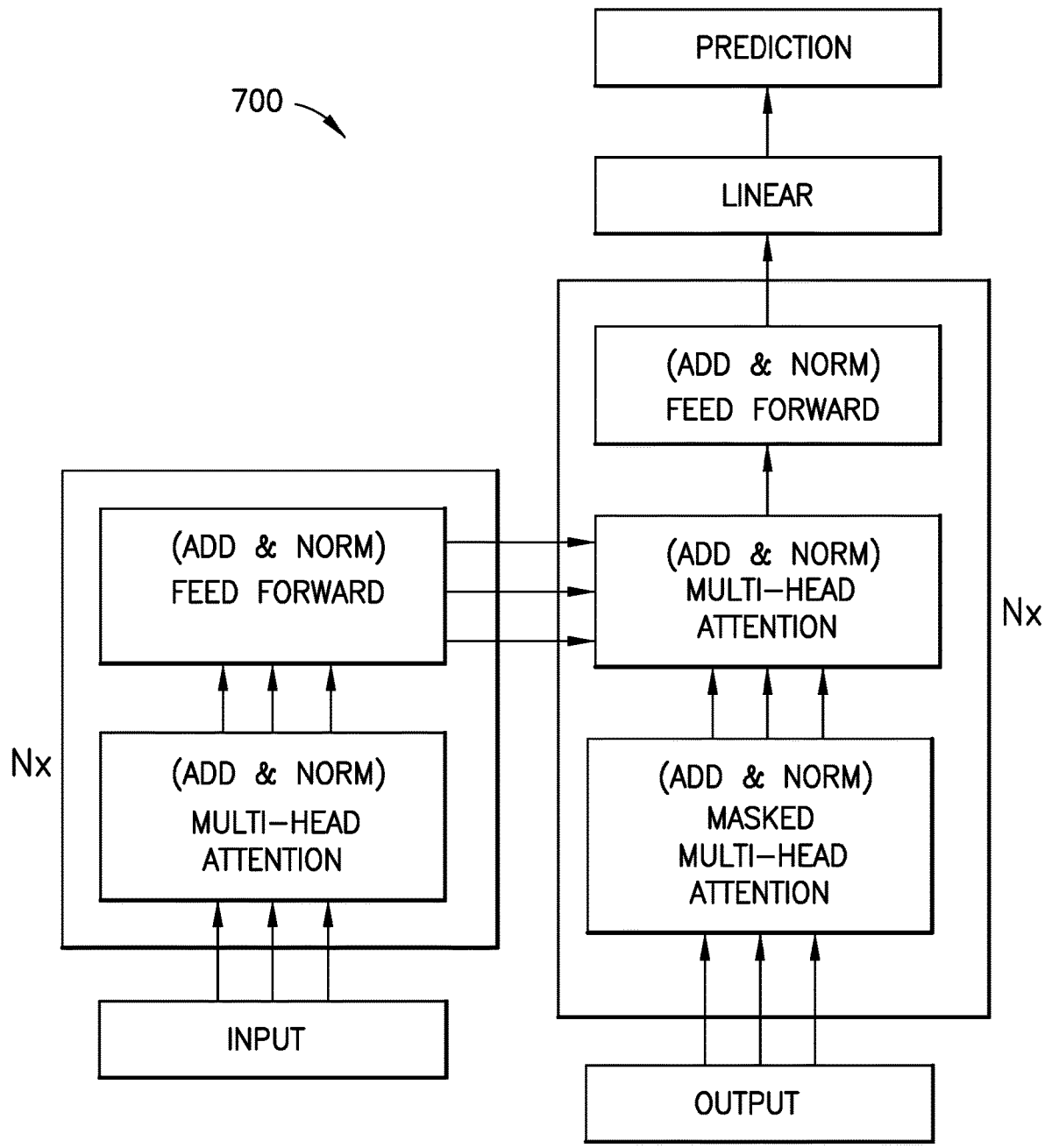
FIG. 7 illustrates the overall structure of a transformer model.

The attention function is performed in parallel. In some implementations, residual connections and dropout may be used in the Transformer model to improve performance. In the context of the present disclosure, since the Transformer model is being applied to a numeric time series, the absolute position in the input may be used instead of positional embedding. The overall structure 700 of a Transformer model is illustrated in the FIG. 7. As shown, the encoder contains one multi-head attention layer and one fully connected layer and the decoder contains one masked multi-head attention layer, one multi-head attention layer and one fully connected layer. Additional information regarding the Transformer model can be found in Vaswani et al., *Attention Is All You Need*, arXiv:1706.03762v5, 2017, which is incorporated herein by reference.

Figure 8:
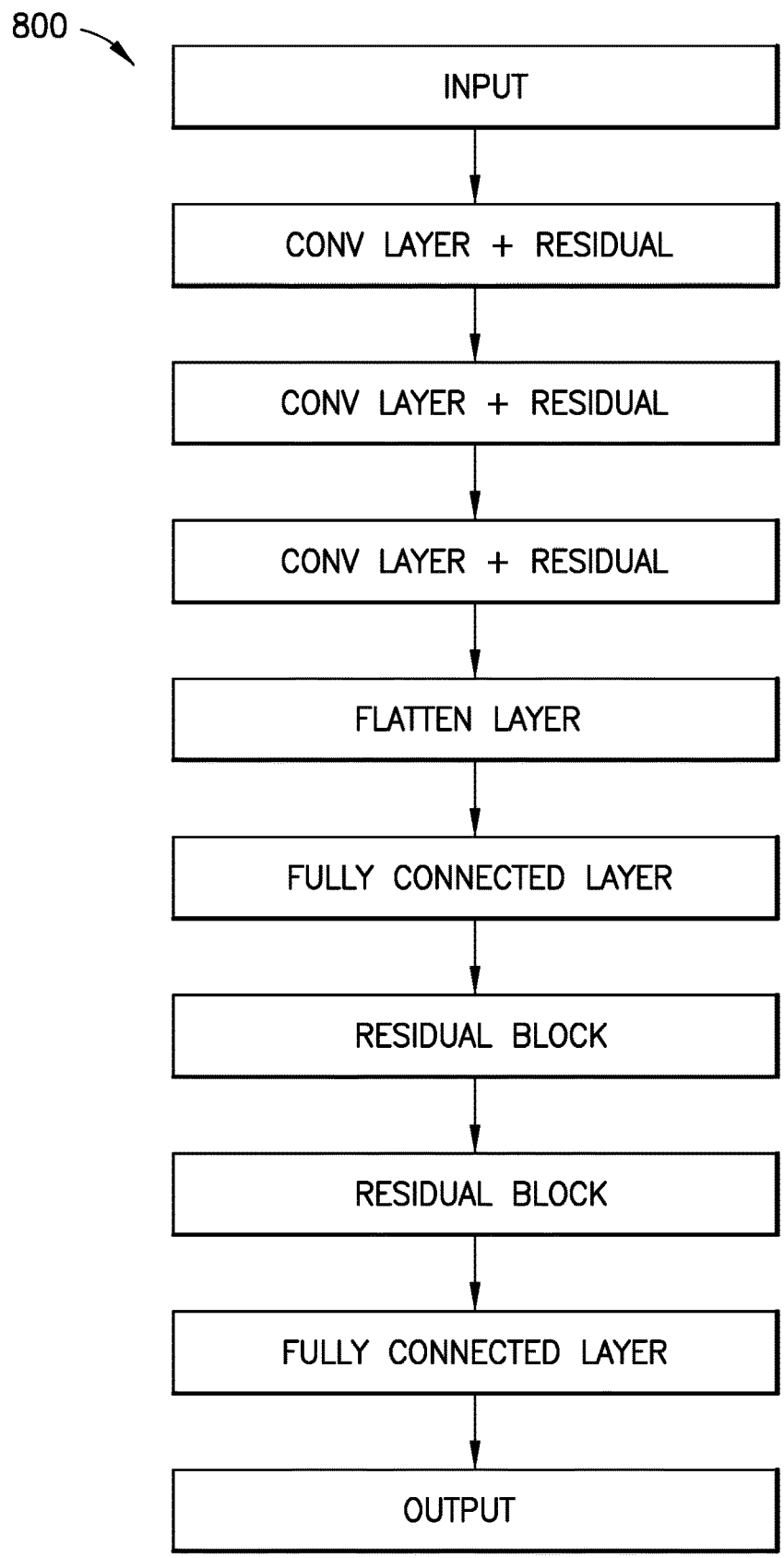
FIG. 8 illustrates the overall structure of a temporal convolutional neural network.

The TCN model has a convolutional hidden layer operating over a one-dimensional sequence. Convolutional neural networks create hierarchical representations over the input sequence in which nearby input elements interact at lower layers while distant elements interact at higher layers. This provides a shorter path to capture long-range dependencies compared to the chain structure modeled by recurrent networks. In some implementations, the overall structure of a TCN model includes several convolutional blocks followed by a flatten layer and several fully connected layers. In some implementations, to equip the model with a sense of order, the absolute position of input elements may be embedded. In some implementations, to avoid the "dead relu" problem, the leaky relu activation function may be applied to each layer of the TCN model. In some implementations, dropout may be used to avoid over fitting. In some implementations, residual connections can be used to improve the performance of the TCN model. The overall structure 800 of a TCN model is illustrated in the FIG. 8. As shown, the TCN model includes multiple convolutional layers followed by a flatten layer and multiple fully connected layers with residual connections. Additional information regarding the TCN model can be found in Bai et al., *An Empirical Evaluation of Generic Convolutional and Recurrent Networks for Sequence Modeling*, arXiv: 1803.01271v2, 2018, which is incorporated herein by reference.

Advantageously, the TCN model has a low memory requirement for training. Table 1 displays the complexity per layer of LMU, LSTM, DNN, Pyramid, TCN, and Transformer models. In Table 1, n is input length, d is model hidden size, and k is kernel size. In the case of a long sequence, such as a 5-minute real-time (RT) input sequence (e.g., having 7500 samples), LSTM models can easily use up all available memory and suffer from the vanishing gradient problem. Furthermore, the Transformer is highly inefficient when the input length is bigger than the model hidden size. In contrast, TCN models can efficiently encode high frequency data.

TABLE 1

| Complexity Per Layer | | | | |
|---|---|---|---|---|
| LMU | LSTM | DNN | TCN/Pyramid | Transformer |
| O(nd) | O(nd$^2$) | O(d$^2$) | O(knd$^2$) | O(n$^2$d) |

Figure 9:
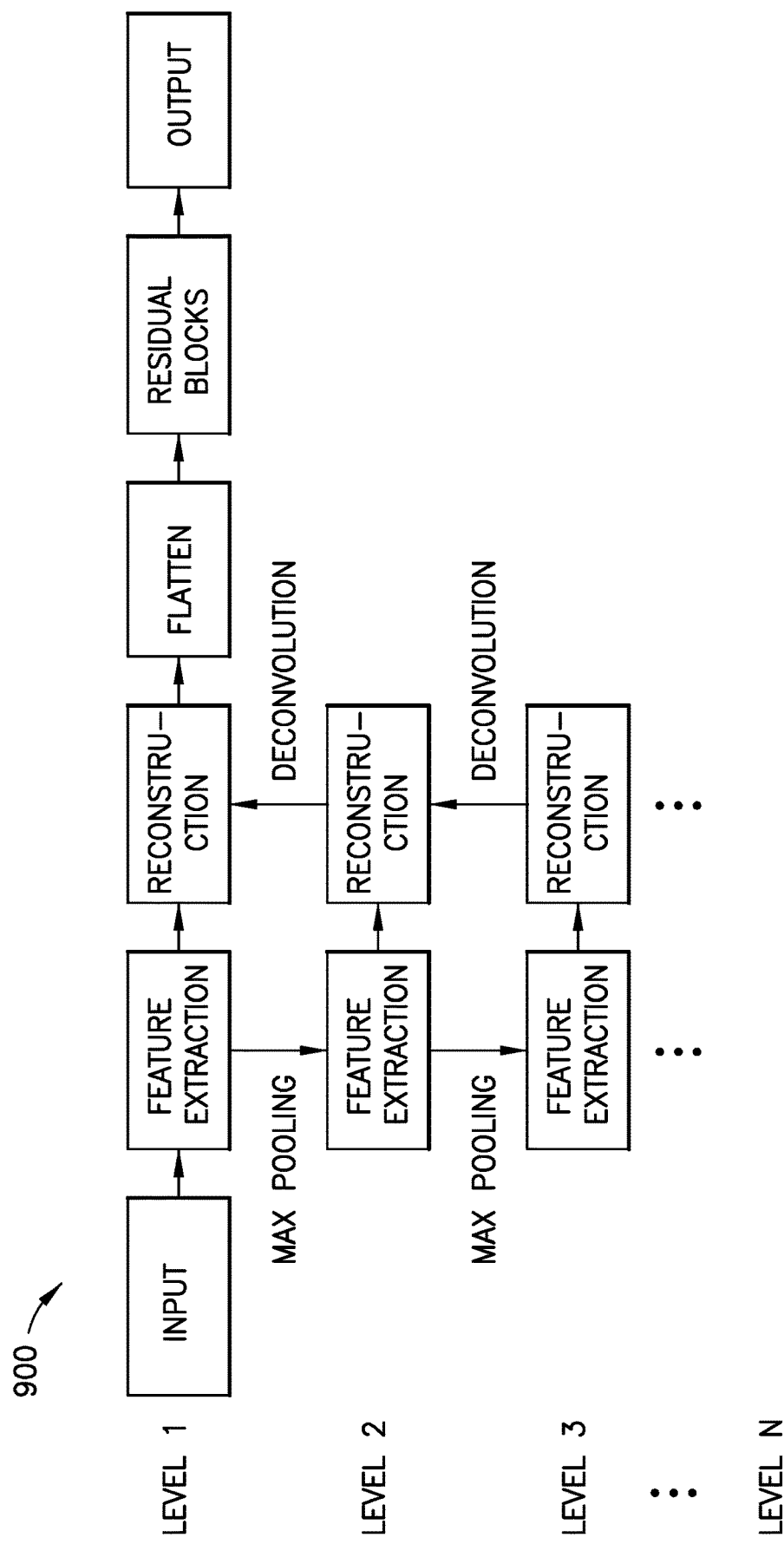
FIG. 9 illustrates the overall structure of a temporal convolutional neural pyramid.

In a Convolutional Neural Pyramid model, a cascade of features is learned in two streams. The first stream across different pyramid levels enlarges the receptive field. The second stream learns information in each pyramid level and finally merges it to produce the final result. As shown in FIG. 9, a structure 900 of a Convolutional Neural Pyramid model includes levels from 1 to N, where N is the number of levels. We denote these levels as $L_i$ where $i \in \{1, \ldots, N\}$. Different-scale content is encoded in each level $L_i$. The feature extraction and reconstruction operations are applied to each level respectively. The input to $L_i$ is the feature extracted from $L_{(i-1)}$ 1) after downsampling. At level $L_i$, 2i convolution layers are used to feature extraction. Then the reconstruction operation fuses information from two neighboring levels. For instance, for $L_i$ and $L_{i+1}$, the output of $L_{i+1}$ is upsampled and then fused with the output from $L_i$. In some implementations, the downsampling operation is implemented as a maxpooling layer and upsampling operation is implemented as a deconvolution layer. Additional information regarding the Convolutional Neural Pyramid model can be found in Shen et al., *Convolutional Neural Pyramid for Image Processing*, arXiv:1704.02071v1 [cs.CV], 2017, which is incorporated herein by reference.

To test the effectiveness of some of the deep learning algorithms described above at predicting an intra-aortic pressure, patient data from 67 transvalvular micro-axial heart pump cases was obtained. Fifty-seven of these cases were indicated for HR-PCI (41 elective, 16 urgent). The remaining 10 were indicated for acute myocardial infarction (AMI) cardiogenic shock (CGS). Additionally, another batch of 17 transvalvular micro-axial heart pump cases were used to compare the performance with respect to the amount of data.

Figure 10:
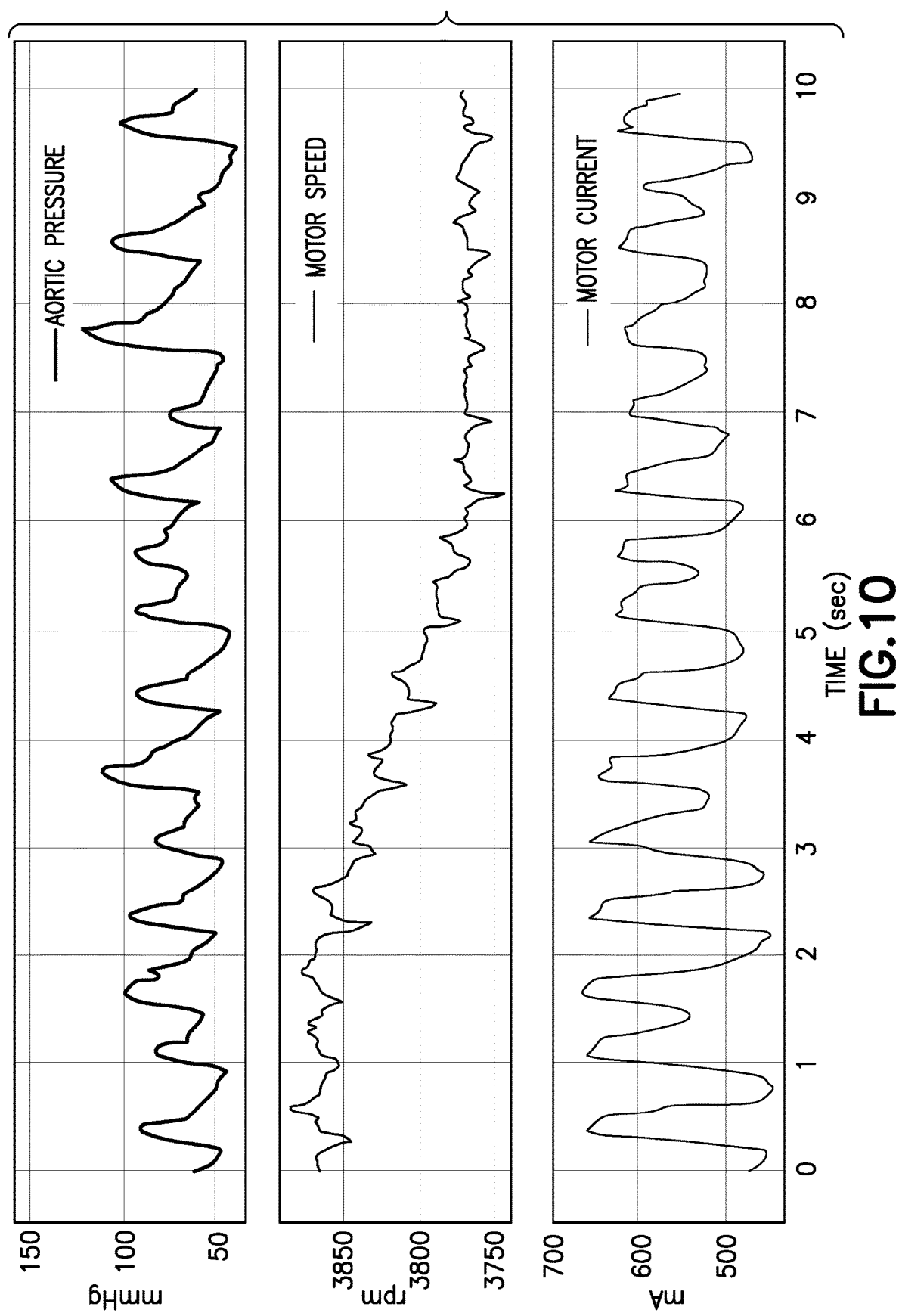
FIG. 10 illustrates 10-second 25 HZ(RT) intra-aortic pressure, motor speed and motor current time series.
Figure 11:
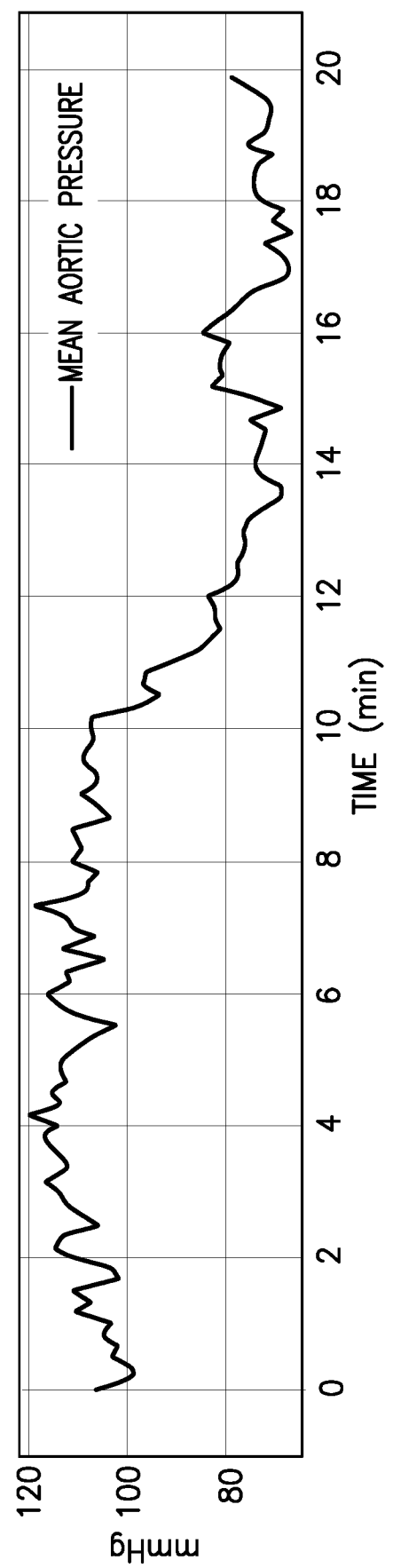
FIG. 11 illustrates a 20-minute 0.1 HZ(AT) mean intra-aortic pressure time series.

The data from these cases included 25 HZ intra-aortic pressure, 25 HZ motor current, 25 HZ motor speed, and other waveforms (e.g., motor speed settings, left ventricular pressure, and heart rate) derived from these three signals. The data was captured by medical device controllers (e.g., controller 130) connected to the transvalvular micro-axial heart pumps (e.g., transvalvular micro-axial heart pump 110). As used herein, a 25HZ time series is referred to as real-time (RT) data. Averaged time (AT) data was derived from the RT data by averaging every 250 RT data points. In other implementations, different quantities of RT data points may be average together to obtain AT data. In some implementations, the quantity of RT data points may be selected based on the desired timescale of the prediction. FIG. 10 illustrates a 10-second sample of a 25 HZ RT Intra-Aortic Pressure and Motor Speed time series. FIG. 11 illustrates a 20-minute sample of a 0.1 HZ AT Intra-Aortic Pressure time series. As shown, the waveform of average intra-aortic pressure is nonstationary and capable of indicating long-term trends of intra-aortic pressure and a patient's physical conditions.

Since features such as, motor speed settings, left ventricular pressure, and heart rate, can be derived from motor speed and intra-aortic pressure, only motor speed and intra-aortic pressure were used to test the effectiveness of some of the deep learning algorithms described above. Motor current was also not included as a feature because the average sequence contains less variation in motor current than motor speed and intra-aortic pressure. However, in other implementations, any of these data sets may be use along with or instead of motor speed and/or intra-aortic pressure.

A sliding window was used to generate sequences of 15,000 samples (10 mins). Sequences where sensor artifacts were not reflective of physiological MAPs (i.e. less than 50 mmHg, greater than 200 mmHg) were removed. A change in intra-aortic pressure greater than 10 mmHg was considered significant. These time series were categorized into three types: increasing sequences (I), decreasing sequences (D), and stationary sequences (S). The overall changes of both increasing sequences and decreasing sequences were greater than 10 mmHg, and the overall changes of stationary sequences were less than 10 mmHg. Ultimately, 50,705 increasing RT sequences, 50,577 decreasing RT sequences, and 419,559 stationary RT sequences were collected. All of these sequences were also converted to 0.1 HZ AT sequences of length 60.

Ten deep learning algorithms (i.e., ARIMA with averaged time (AT) input, DNN with AT input, LMU with AT input, LSTMs with AT input, LSTMs with Attention with AT input, TCN with real-time (RT) input, TCN with AT input, Transformer with AT input, Pyramid with AT input, and Pyramid with RT input) were trained to predict mean intra-aortic pressure (MAP) five minutes in advance. In other implementations, the forecasting window may be increased or decreased. For example, in other implementations, the forecasting window may be increased to 10 or 15 minutes. The ten deep learning algorithms were also trained using RMSprop optimizer and a learning rate decay of 0.8. A 60%-20%-20% training-validation-test split was used. Since there are many possible combinations of hyper-parameters, a hyper-parameter random grid search was performed on a 10% hold out dataset. See, e.g., Bergstra & Bengio, *Random Search for Hyper-Parameter Optimization*, Journal of Machine Learning Research 13 281-305, 2012. The hyper-parameter search ranges can be found in Table 2. A Root Mean Squared Error (RMSE) was used as an evaluation metric. A computed moving average of RMSE on the validation set was used as an early stopping criteria. The same batch size of 64 was used for all tests.

TABLE 2

| | Hyper-Parameter Random Search Range | | | | | |
|---|---|---|---|---|---|---|
| ARIMA | #Moving Average 0~3 | #Lags 1~10 | #Differenced 0~3 | | | |
| LMU | Learning Rate 0.1~0.00001 | #Layers 0~9 | Hidden Size 64~512 | | | |
| NN | Learning Rate 0.1~0.00001 | #Layers 0~9 | Hidden Size 64~512 | | | |
| LSTMs (Attention) | Learning Rate 0.1~0.00001 | Dropout Rate 0~0.9 | #Encoder Layer 1~3 | #Decoder Layer 1~3 | Hidden Size 64~512 | |
| TCN | Learning Rate 0.1~0.00001 | Dropout Rate 0~0.9 | #Encoder Layer 2~9 | #Decoder Layer 2~9 | Hidden Size 64~512 | |
| Transformer | Learning Rate 0.1~0.00001 | Dropout Rate 0~0.9 | Model Size 64~512 | FF Size 64~512 | #Layers 2~6 | #Heads 2~8 |
| Pyramid | Learning Rate 0.1~0.00001 | Dropout Rate 0~0.9 | Hidden Size 64~512 | #Decoder Layer 1~5 | #Mapping Layer 1~3 | #Levels 2~6 |

Figure 12:
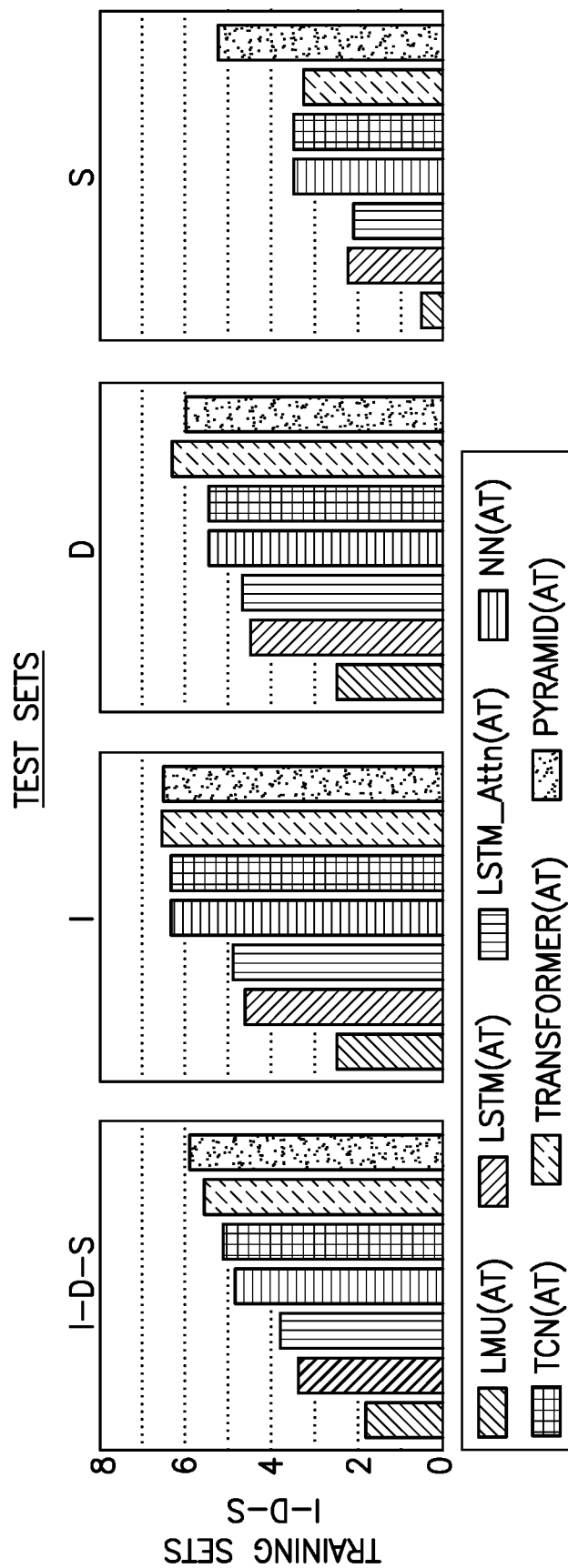
FIG. 12 illustrates the root-mean-square error of select models.

FIG. 12 provides a comparison of the average RMSEs achieved by some of the tested deep learning algorithms. From left to right, each of the bar plots provides the average RMSE achieved by LMU with AT input, LSTM with AT input, LSTM with Attention with AT input, DNN with AT input, TCN with AT input, Transformer with AT input, and Pyramid with AT input. As shown, the models were tested on an increasing (I) only dataset, a decreasing (D) only dataset, a stationary (S) only dataset, and an I-D-S dataset. The I-D-S dataset contained equal proportions of all three types of sequences. 50,000 sequences of samples were included in the I, D, and S datasets. 150,000 sequences of samples were included in the I-D-S datasets. All of the models were trained on an I-D-S dataset. Overall, the LMU model consistently achieved the best average RMSE scores, including an average RMSE of 1.837 mmHg on the I-D-S dataset.

Figure 13:
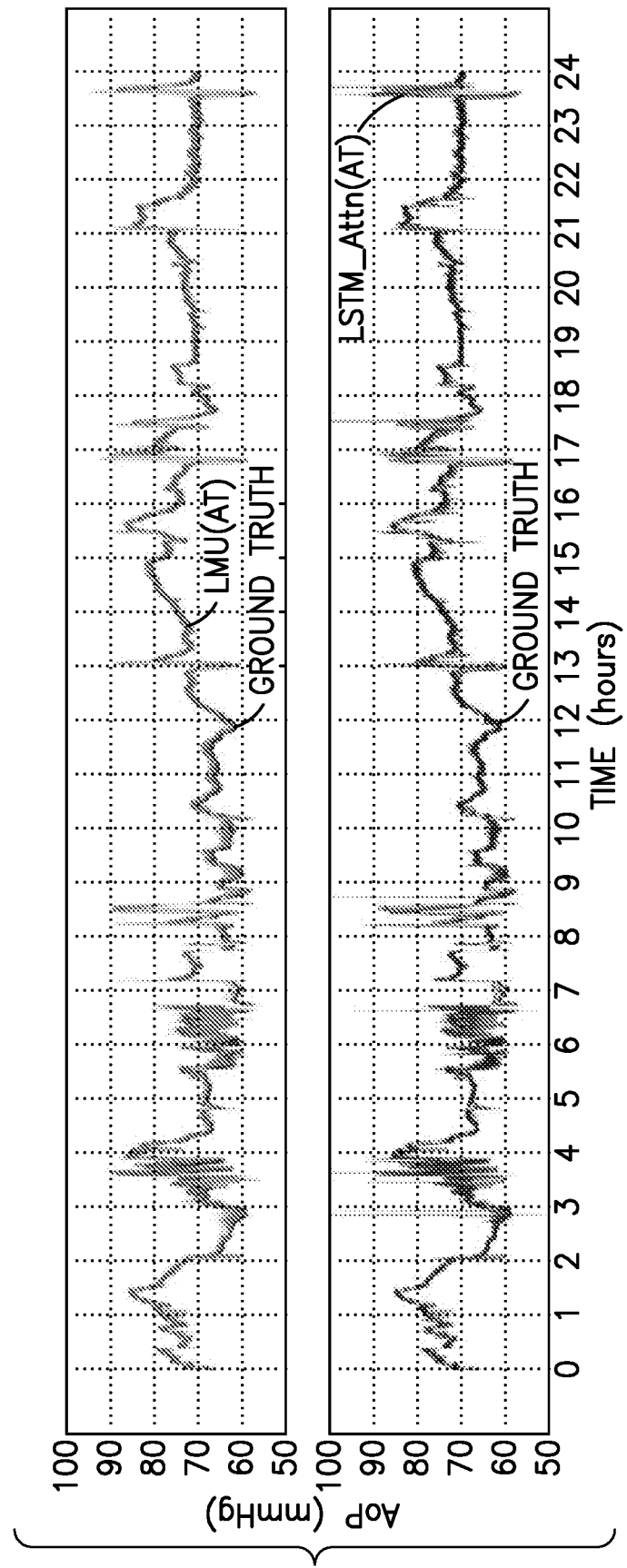
FIG. 13 illustrates the MAP forecasts of two deep learning models against the ground truth for a single recording over the course of 24 hours.
Figures 14, 14A, 14B:
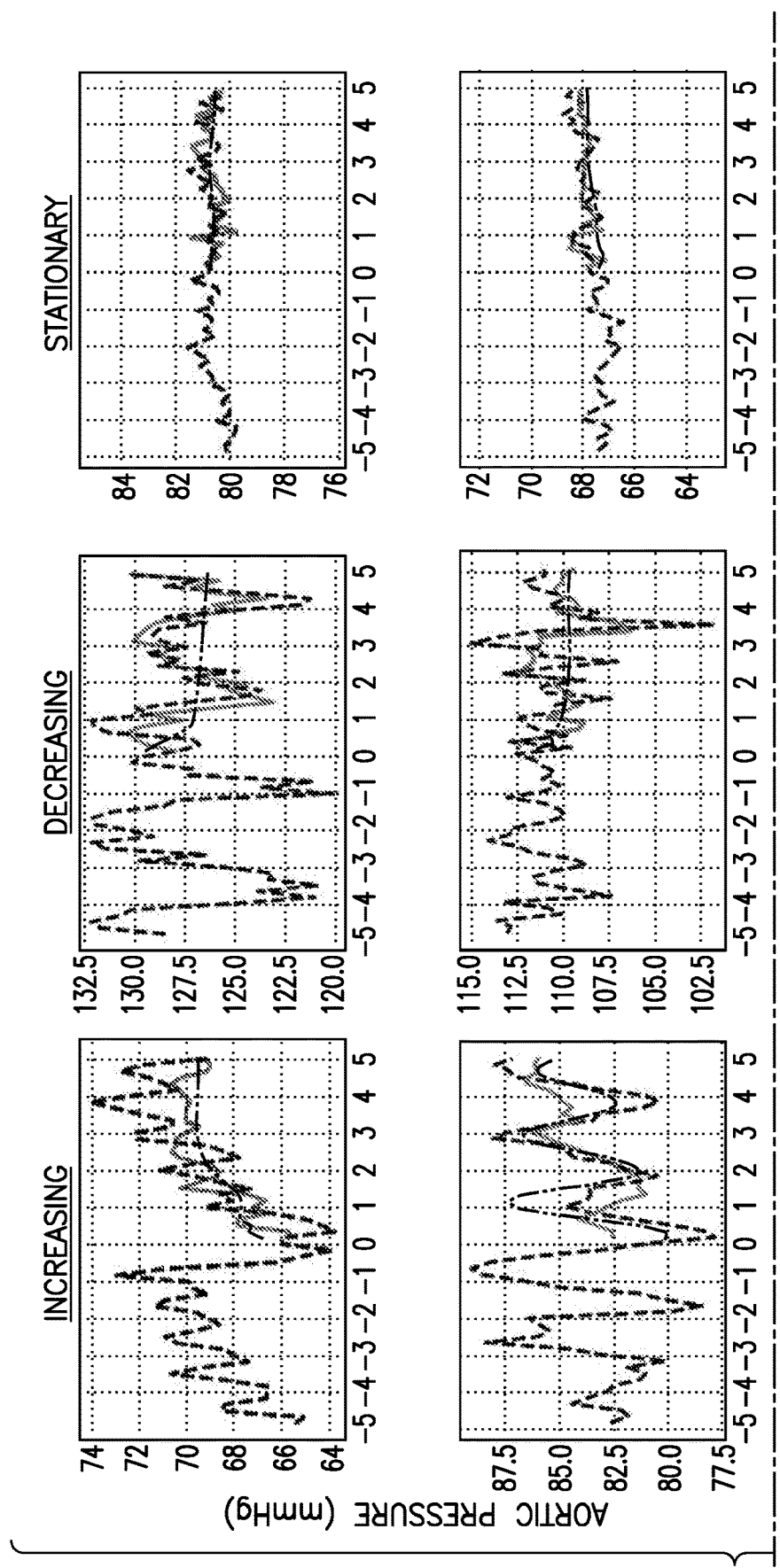
FIG. 14 illustrates the MAP forecasts of two deep learning models on increasing sequences, decreasing sequences and stationary sequences.
Figure 14B:
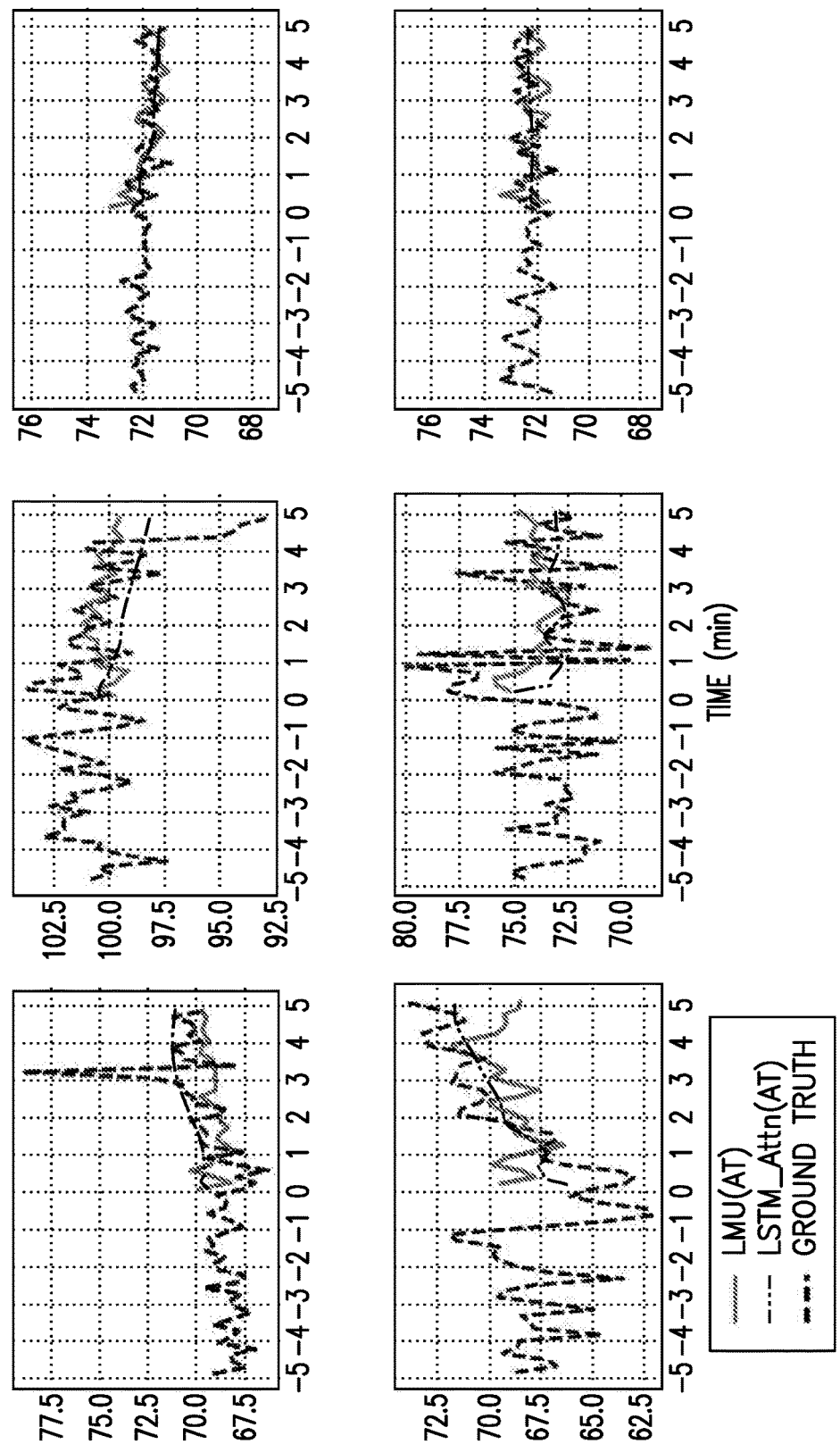

FIGS. 13 and 14 illustrate the MAP forecasts generated by the two top-performing models, LMU with AT input and LSTM with Attention with AT input. FIG. 13 illustrates the MAP forecasts against the ground truth (e.g., the true intra-aortic pressure) for a single recording over the course of 24 hours. The black line is the ground truth and the colored lines are the model predictions. FIG. 14 illustrates the MAP forecasts on increasing sequences, decreasing sequences and stationary sequences. The dashed line is the ground truth and the solid lines are the model predictions.

The prior five minutes of intra-aortic pressure and motor speed are the inputs to generate the predicted intra-aortic pressure values. As shown, both models closely follow the ground truth.

Table 3 displays all RMSE values (mmHg) per cohort for the models trained on permutations of the Increasing-Decreasing-Stationary (I, D, S) data sets. The top number in each entry is the RMSE result of the combined cohort. The three values in parenthesis are RMSEs on each of three test sets, which only contained increasing, decreasing, and stationary sequences, respectively. All results are averages of five runs. The I-D-S training set contained equal proportions of all three types of sequences. The I-D only training set contained equal proportions of increasing sequences and decreasing sequences. The I-S only training set contained equal proportions of increasing sequences and stationary sequences. The D-S only training set contained equal proportions of decreasing sequences and stationary sequences.

Figures 15, 15A:
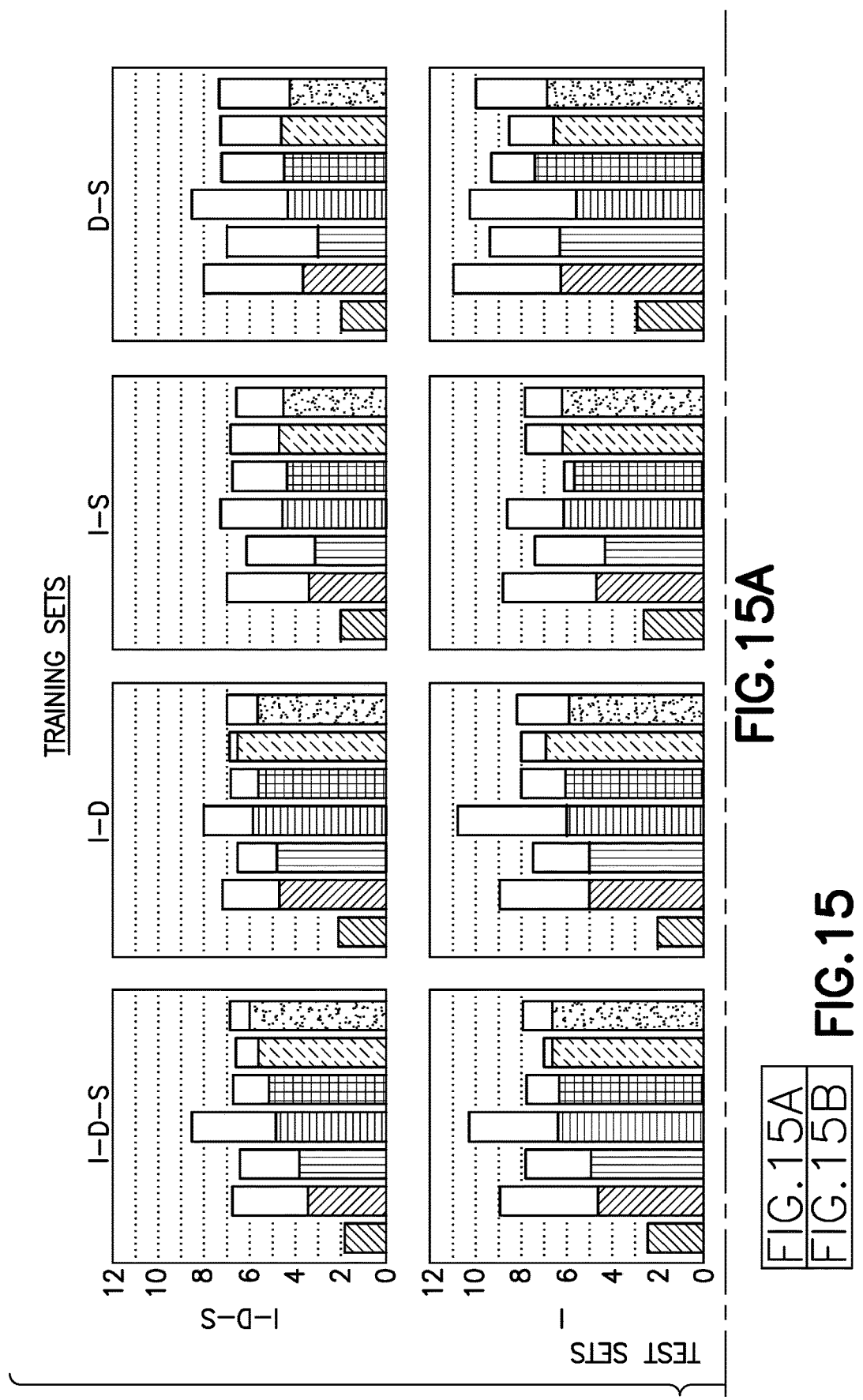
FIG. 15 illustrates the root-mean-square error of select models.
Figure 15B:
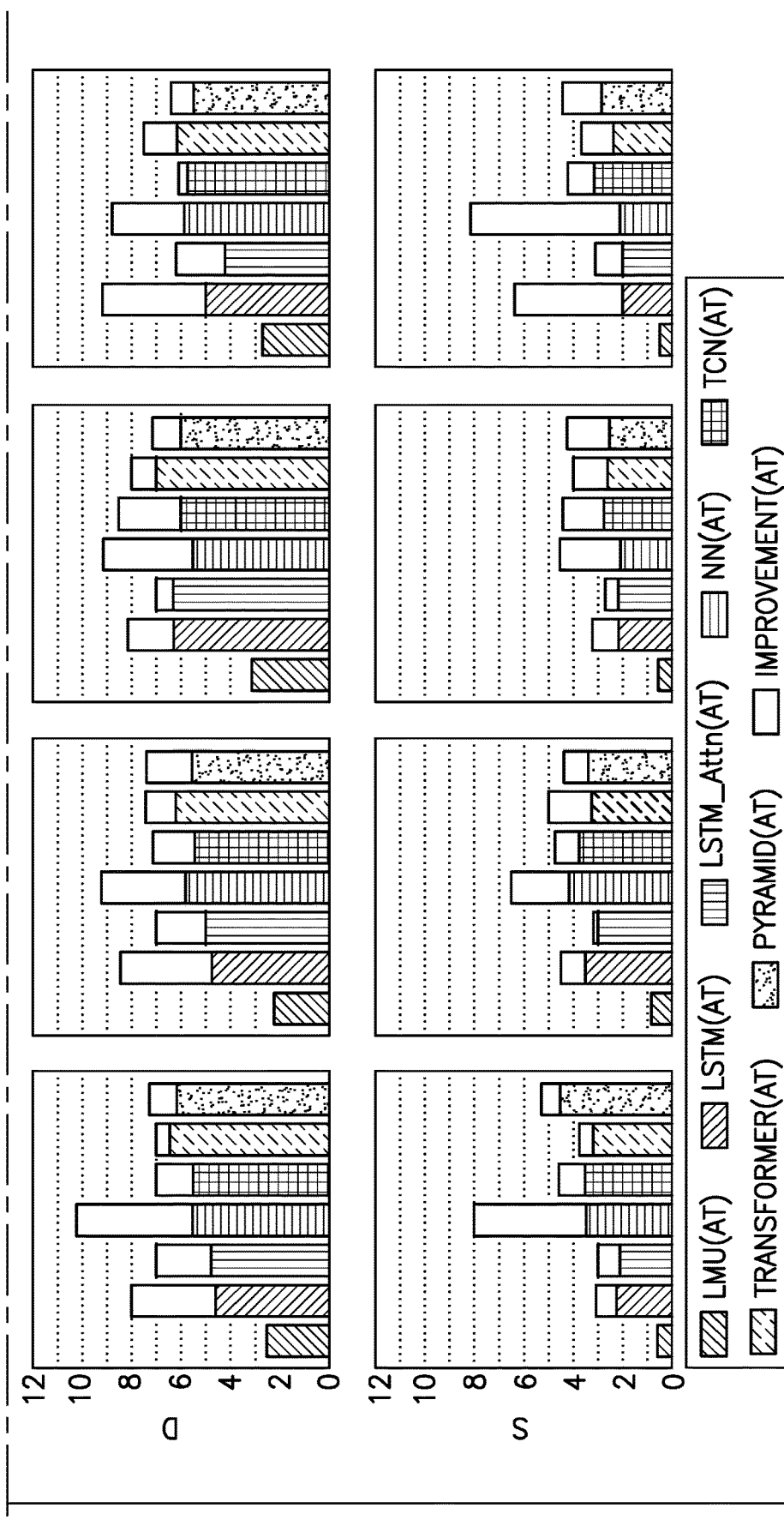

FIG. 15 provides a comparison of the average RMSEs achieved by some of the tested deep learning algorithms. From left to right, each of the bar plots provides the average RMSE achieved by LMU with AT input, LSTM with AT input, LSTM with Attention with AT input, DNN with AT input, TCN with AT input, Transformer with AT input, and Pyramid with AT input. Different training and test datasets were used with these models. The light gray portion of each bar represents the prediction performance improvement between the initial patient cohort (N=20) and the current patient cohort (N=67). Each model was trained on permutations of the Increasing-Decreasing-Stationary (I, D, S) data sets, as described above in relation to Table 3. Furthermore, each model was tested on an increasing (I) only dataset, a decreasing (D) only dataset, a stationary (S) only dataset, and an I-D-S dataset, as described above in relation to FIG. 12. Without stationary sequences in the training set, all models can achieve comparable or even better performance for predicting stationary sequences. Furthermore, the improvement illustrated above each bar demonstrates a potential for even better model performance as more data is collected in the future.

TABLE 3

| Models\Training Sets | I-D-S | I-D | I-S | D-S |
|---|---|---|---|---|
| ARIMA (AT) | 15.943 (10.151-10.089-7.894) | 13.999 (10.713-9.11-6.444) | 19.16 (8.556-9.068-4.549) | 16.73 (10.176-8.703-8.058) |
| NN (AT) | 4.842 (6.337-5.434-3.488) | 5.809 (5.968-5.73-4.111) | 4.519 (6.116-5.393-2.094) | 4.39 (5.525-5.756-2.118) |
| LMU (AT) | 1.837 (2.507-2.491-0.545) | 2.143 (2.111-2.19-0.825) | 2.079 (2.621-3.088-0.572) | 2.011 (2.901-2.64-0.491) |
| LSTM (AT) | 3.363 (4.577-4.468-2.211) | 4.603 (4.92-4.619-3.508) | 3.359 (4.609-6.131-2.064) | 3.638 (6.17-4.789-2.041) |
| LSTM_Attention (AT) | 3.799 (4.904-4.686-2.102) | 4.746 (5.031-4.841-3.158) | 3.118 (4.323-6.161-2.139) | 3.07 (6.262-4.159-2.057) |
| TCN (AT) | 5.153 (6.337-5.434-3.488) | 5.603 (6.031-5.349-3.714) | 4.383 (5.709-5.95-2.741) | 4.543 (7.337-5.664-3.131) |
| Pyramid (AT) | 5.947 (6.555-6.056-5.231) | 5.587 (5.841-5.444-3.333) | 4.489 (6.146-5.98-2.485) | 4.236 (6.799-5.341-2.793) |
| Transformer (AT) | 5.589 (6.57-6.352-3.223) | 6.492 (6.888-6.095-4.968) | 4.7 (6.146-6.884-2.561) | 4.605 (6.508-6.047-2.348) |
| TCN (RT) | 6.555 (6.757-6.804-4.686) | 7.158 (8.142-7.126-5.619) | 6.854 (6.869-7.983-4.835) | 7.413 (9.7-6.293-5.111) |
| Pyramid (RT) | 7.224 (7.8-7.271-5.838) | 7.777 (9.682-6.714-5.714) | 6.628 (7.411-6.688-4.504) | 7.597 (9.316-6.63-6.001) |

Overall, these test results demonstrate that the systems and methods described above can be used to accurately predict an intra-aortic pressure of a patient. Advance warning of imminent changes in the intra-aortic pressure of a patient, even if the warning comes only 5 to 15 minutes ahead, can greatly enhance clinical outcomes. For example, the authors of Wijnberge et al., *Effect of a Machine Learning-Derived Early Warning System for Intraoperative Hypotension vs Standard Care on Depth and Duration of Intraoperative Hypotension During Elective Noncardiac Surgery: The HYPE Randomized Clinical Trial*, JAMA, Caring for the Critically Ill Patient, doi:10.1001/jama.2020.0592, 2020 observed that significantly less time spent in hypotensive events during surgery when a machine learning warning system was used to inform clinicians of possible hypotension. Being able to forecast significant changes (e.g., +/−10 mmHg) in intra-aortic pressure and notifying caregivers gives clinicians time to appropriately intervene before hemodynamic instability occurs. Additionally, intra-aortic pressure forecasting can aid in weaning a patient from mechanical circulatory support following native heart recovery. Since the level of hemodynamic support can be varied by altering the motor speed of the transvalvular pump, advance forecasting of MAP can also aid in maintenance/escalation of hemodynamic support.

From the foregoing and with reference to the various figure drawings, those skilled in the art will appreciate that certain modifications can also be made to the present disclosure without departing from the scope of the same. While several implementations of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular implementations. Those skilled in the art will envision other modifications within the scope and spirit of the claims appended hereto.

The invention claimed is:

1. A system comprising:
   a transvalvular micro-axial heart pump comprising a motor and a pressure sensor; and
   one or more processors configured to:
      obtain a set of intra-aortic pressure measurements corresponding to pressure values measured by the pressure sensor during a period of time when the transvalvular micro-axial pump is at least partially located in a patient's heart;
      obtain a set of motor speed measurements corresponding to rotational speeds of the motor during the period of time;
      predict, using a trained machine learning model, an intra-aortic pressure of a patient based on the sets of intra-aortic pressure and motor speed measurements; and automatically adjust a speed setting of the motor based on the predicted intra-aortic pressure of the patient.

2. The system of claim 1, wherein the one or more processors are further configured to obtain a set of current measurements corresponding to an energy intake of the motor during the period of time, and wherein the prediction is further based on the set of current measurements.

3. The system of claim 1, wherein the transvalvular micro-axial heart pump further comprises a tube, an inlet area having one or more openings through which blood may be drawn into the tube by the motor, and an outlet area having one or more openings through which blood may be expelled from the tube by the motor, and wherein the pressure sensor is coupled to the outlet area.

4. The system of claim 3, wherein the transvalvular micro-axial heart pump further comprises an additional pressure sensor coupled to the inlet area, wherein the one or more processors are further configured to obtain a set of left ventricular pressure measurements corresponding to pressure values measured by the additional pressure sensor during the period of time, and wherein the prediction is further based on the set of left ventricular pressure measurements.

5. The system of claim 1, wherein the machine learning model is a deep learning model.

6. The system of claim 5, wherein the deep learning model is an Autoregressive Integrated Moving Average (ARIMA) model, a Deep Neural Network (DNN) model, a Recurrent Sequence to Sequence model, a Recurrent Sequence to Sequence model with Attention, a Transformer model, a Temporal Convolutional Neural Network (TCN) model, or a Convolutional Neural Pyramid model.

7. The system of claim 5, wherein the deep learning model is a Recurrent Sequence to Sequence model with a Legendre Memory Unit (LMU).

8. The system of claim 1, wherein the machine learning model is trained on a data set comprising increasing sequences, decreasing sequences, and stationary sequences, and wherein each sequence comprises intra-aortic pressure and motor speed measurements.

9. The system of claim 8, wherein a sequence is increasing if the intra-aortic pressure measurements within that sequence increase by more than a predetermined threshold, wherein a sequence is decreasing if the intra-aortic pressure measurements within that sequence decrease by more than the predetermined threshold, and wherein a sequence is stationary if the intra-aortic pressure measurements within that sequence do not increase or decrease by more than the predetermined threshold.

10. The system of claim 9, wherein the predetermined threshold is 10 mmHg.

11. The system of claim 8, wherein each sequence comprises a predetermined number of aortic pressure and motor speed measurements.

12. The system of claim 8, wherein each sequence comprises real-time (RT) intra-aortic pressure and motor speed measurements.

13. The system of claim 8, wherein each sequence comprises average time (AT) intra-aortic pressure and motor speed measurements.

14. The system of claim 1, wherein the machine learning model is trained on a data set comprising only increasing and decreasing sequences, and wherein each sequence comprises intra-aortic pressure and motor speed measurements.

15. The system of claim 13, wherein a sequence is increasing if the intra-aortic pressure measurements within that sequence increase by more than a predetermined threshold, and wherein a sequence is decreasing if the intra-aortic pressure measurements within that sequence decrease by more than the predetermined threshold.

16. The system of claim 1, wherein automatically adjusting the speed setting of the motor based on the predicted intra-aortic pressure of the patient comprises temporarily increasing the speed setting of the motor when the predicted intra-aortic pressure of the patient is less than a current intra-aortic pressure of the patient by more than a predetermined amount.

17. A system comprising:
 a transvalvular micro-axial heart pump comprising a motor and a pressure sensor;
 one or more processors configured to:
  obtain a set of intra-aortic pressure measurements corresponding to pressure values measured by the pressure sensor during a period of time when the transvalvular micro-axial pump is at least partially located in a patient's heart;
  obtain a set of motor speed measurements corresponding to rotational speeds of the motor during the period of time; and
  predict, using a trained machine learning model, an intra-aortic pressure of the patient based on the sets of intra-aortic pressure and motor speed measurements; and
 a display configured to display the predicted intra-aortic pressure of the patient.

18. The system of claim 17, wherein the display is configured to simultaneously display the predicted intra-aortic pressure of the patient with a current intra-aortic pressure of the patient and a current speed setting of the motor.

19. The system of claim 17, wherein the display is further configured to display an alert when the predicted intra-aortic pressure of the patient is less than a current intra-aortic pressure of the patient by more than a predetermined amount.

20. The system of claim 17, wherein the display is configured to display the predicted intra-aortic pressure of the patient as part of a graph.

21. A method for treating a patient with a transvalvular micro-axial heart pump received into the patient's body, the method comprising:
 inserting a transvalvular micro-axial heart pump into the body of a patient;
 obtaining a set of intra-aortic pressure measurements corresponding to pressure values measured by a pressure sensor located on the transvalvular micro-axial heart pump during a period of time when the transvalvular micro-axial pump is at least partially located in the patient's heart;
 obtaining a set of motor speed measurements corresponding to rotational speeds of the motor during the period of time;
 predicting, using a trained machine learning model, an intra-aortic pressure of the patient based on the sets of intra-aortic pressure and motor speed measurements; and
 automatically adjusting a speed setting of the motor based on the predicted intra-aortic pressure of the patient.

22. The method of claim 21 further comprising obtaining a set of current measurements corresponding to an energy intake of the motor during the period of time, and wherein the prediction is further based on the set of current measurements.

23. The method of claim 21 wherein the transvalvular micro-axial heart pump further comprises a tube, an inlet area having one or more openings through which blood may be drawn into the tube by the motor, and an outlet area having one or more openings through which blood may be expelled from the tube by the motor, and wherein the pressure sensor is coupled to the outlet area.

24. The method of claim 23, wherein the transvalvular micro-axial heart pump further comprises an additional pressure sensor coupled to the inlet area, wherein the method further comprises obtaining a set of left ventricular pressure measurements corresponding to pressure values measured by the additional pressure sensor during the period of time, and wherein the prediction is further based on the set of left ventricular pressure measurements.

25. The method of claim 21 further comprising:
adjusting an amount of a medication provided to the patient based on the predicted intra-aortic pressure.

26. The method of claim 21 further comprising:
decreasing the motor speed if the intra-aortic pressure is predicted to increase.

27. The method of claim 21 further comprising:
increasing the motor speed if the intra-aortic pressure is predicted to decrease.

* * * * *

UNITED STATES PATENT AND TRADEMARK OFFICE
CERTIFICATE OF CORRECTION

| | |
|---|---|
| PATENT NO. | : 11,581,083 B2 |
| APPLICATION NO. | : 16/889457 |
| DATED | : February 14, 2023 |
| INVENTOR(S) | : Ahmad El Katerji et al. |

It is certified that error appears in the above-identified patent and that said Letters Patent is hereby corrected as shown below:

In the Drawings

Sheet 11 of 25, Fig. 3, Reference No. 346:
Now reads: "OSR"; should read -- OCR --

In the Specification

Column 7, Line 16:
Now reads: "canula"; should read -- cannula --

Column 9, Line 6:
Now reads: "100"; should read -- 110 --

Column 9, Line 11:
Now reads: "100"; should read -- 110 --

Column 9, Line 14:
Now reads: "100"; should read -- 110 --

Column 9, Line 45:
Now reads: "100"; should read -- 110 --

Column 9, Line 53:
Now reads: "161"; should read -- 261 --

Column 18, Line 37:
Now reads: "1) after"; should read -- after --

Signed and Sealed this
Twenty-seventh Day of June, 2023

Katherine Kelly Vidal
*Director of the United States Patent and Trademark Office*